(12) United States Patent
Polak et al.

(10) Patent No.: US 12,027,254 B2
(45) Date of Patent: Jul. 2, 2024

(54) MULTI-CONTRAST MRI IMAGE RECONSTRUCTION USING MACHINE LEARNING

(71) Applicants: Siemens Healthcare GmbH, Erlangen (DE); The General Hospital Corporation, Boston, MA (US)

(72) Inventors: Daniel Polak, Erlangen (DE); Kawin Setsompop, Charlestown, MA (US)

(73) Assignee: Siemens Healthineers AG, Erlangen (DE)

(*) Notice: Subject to any disclaimer, the term of this patent is extended or adjusted under 35 U.S.C. 154(b) by 290 days.

(21) Appl. No.: 17/179,999

(22) Filed: Feb. 19, 2021

(65) Prior Publication Data

US 2021/0264645 A1 Aug. 26, 2021

Related U.S. Application Data

(60) Provisional application No. 62/979,853, filed on Feb. 21, 2020.

(51) Int. Cl.
*G06K 9/00* (2022.01)
*A61B 5/055* (2006.01)
(Continued)

(52) U.S. Cl.
CPC ............ *G16H 30/40* (2018.01); *A61B 5/055* (2013.01); *G06F 18/214* (2023.01); *G06F 18/22* (2023.01);
(Continued)

(58) Field of Classification Search
CPC . G06T 11/006; G06T 7/30; G06T 7/20; G06T 2207/10088; G06T 2207/20081;
(Continued)

(56) References Cited

U.S. PATENT DOCUMENTS

| | | | |
|---|---|---|---|
| 11,181,598 B2* | 11/2021 | Polak | A61B 5/055 |
| 2016/0113501 A1* | 4/2016 | Hua | A61B 5/0042 |
| | | | 600/420 |

(Continued)

OTHER PUBLICATIONS

Akçakaya M., Moeller S., Weingärtner S., Ugurbil K., "Scan-specific robust artificialneural-networks for k-space interpolation (RAKI) reconstruction: Database-free deep learning for fast imaging", in: Magn. Reson. Med., vol. 81, No. 1, pp. 439-453; 2019.

(Continued)

*Primary Examiner* — Emily C Terrell
*Assistant Examiner* — Kevin M Coomber
(74) *Attorney, Agent, or Firm* — Banner & Witcoff Ltd.

(57) ABSTRACT

A method for reconstructing a MRI image may include: receiving MRI measurement data sets $f_1$ to $f_N$, each data set being acquired from an examination object based on a different MRI protocol of an MRI system; receiving MRI images $u_1^o$ to $u_N^o$ corresponding to the MRI measurement data sets $f_1$ to $f_N$; performing one or more translation and rotation transformations on the MRI images $u_1^o$ to $u_N^o$; applying one or more trained functions: to the transformed MRI images $u_1^o$ to $u_N^o$, using a neural network, and to the MRI images $u_1^o$ to $u_N^o$, using a forward-sampling operator; performing one or more inverse translation and rotation transformations on an output of the neural network; and generating at least one output MRI image $u^T$ based on an output of the forward-sampling operator, the inversely transformed output of the neural network, and the input MRI images $u_1^o$ to $u_N^o$.

24 Claims, 8 Drawing Sheets

(51) Int. Cl.
| | |
|---|---|
| *G06F 18/214* | (2023.01) |
| *G06F 18/22* | (2023.01) |
| *G06N 3/08* | (2023.01) |
| *G06T 7/20* | (2017.01) |
| *G06T 7/30* | (2017.01) |
| *G06T 11/00* | (2006.01) |
| *G06V 10/764* | (2022.01) |
| *G06V 10/82* | (2022.01) |
| *G16H 30/40* | (2018.01) |

(52) U.S. Cl.
CPC .............. *G06N 3/08* (2013.01); *G06T 7/20* (2013.01); *G06T 7/30* (2017.01); *G06T 11/006* (2013.01); *G06V 10/764* (2022.01); *G06V 10/82* (2022.01); *G06T 2207/10088* (2013.01); *G06T 2207/20081* (2013.01); *G06T 2207/20084* (2013.01); *G06V 2201/03* (2022.01)

(58) Field of Classification Search
CPC ... G06T 2207/20084; G06T 5/00; G06T 3/00; G06T 3/0006; G16H 30/40; A61B 5/055; G06K 9/6215; G06K 9/6256; G06N 3/08; G06V 2201/03; G06V 10/82; G06V 10/764; G06V 10/70; G06V 10/88; G06V 10/94; H04S 3/00; H04S 5/00; G09G 19/00; G06F 18/22; G06F 18/214; G16B 40/00

See application file for complete search history.

(56) References Cited

U.S. PATENT DOCUMENTS

| | | | | |
|---|---|---|---|---|
| 2017/0309019 A1* | 10/2017 | Knoll | ............... | G01R 33/5611 |
| 2017/0325707 A1* | 11/2017 | Spottiswoode | .. | G01R 33/56509 |
| 2018/0025489 A1* | 1/2018 | Tiwari | ............... | G01R 33/5602 |
| | | | | 600/420 |
| 2019/0066281 A1* | 2/2019 | Zheng | .................... | G06N 3/047 |
| 2019/0139238 A1* | 5/2019 | Wyeth | ........................ | G06T 7/74 |
| 2019/0388123 A1* | 12/2019 | Pavlovskaia | ........... | G06T 19/00 |
| 2020/0143457 A1* | 5/2020 | Manmatha | .......... | G06F 3/04812 |
| 2020/0211188 A1* | 7/2020 | Gao | ........................ | G06N 3/08 |
| 2020/0289019 A1* | 9/2020 | Schlemper | ............. | G06N 3/088 |
| 2020/0341094 A1 | 10/2020 | Polak et al. | | |
| 2021/0063518 A1* | 3/2021 | Zhang | .................... | G06N 3/088 |

OTHER PUBLICATIONS

Moriguchi Hisamoto et al.: "Bunched Phase Encoding (BPE): A New Fast Data Acquisition Method in MRI"; Magnetic Resonance in Medicine 55; p. 633-648; 2006.

Berkin Bilgic et al.: "Wave-CAIPI for highly accelerated 3D imaging", Magnetic Resonance in Medicine., pp. 2152-2162, XP055349786, US ISSN: 0740-3194, DOI: 10.1002/mrm.25347, figure 1, p. 2153-p. 2154, pp. 2156-2157, and p. 2160; 2014.

Jenkinson M., Smith S., "A global optimisation method for robust affine registration of brain images," in: Medical Image Analysis 5, 143-156.; 2001.

Pruessmann, Klaas P. et al., "SENSE: Sensitivity Encoding for Fast MRI," Magnetic Resonance in Medicine, vol. 42, No. 5, pp. 952-962, Nov. 1999 (First published: Oct. 28, 1999) //https://doi.org/10.1002/(SICI)1522-2594(199911)42:5<952::AID-MRM16>3.0.CO;2-S.

Zhu, Bo, et al. "Image reconstruction by domain-transform manifold learning." Nature 555.7697; 2018.

Hammernik, Kerstin et al.: "Learning a Variational Network for Reconstruction of Accelerated MRI Data"; in: Magnetic Resonance in Medicine; vol. 79; pp. 3055-3071; DOI 10.1002/mrm.26977; 2018.

Griswold, Mark A. et al. "Generalized Autocalibrating Partially Parallel Acquisitions (GRAPPA)" Magnetic Resonance in Medicine, vol. 47, pp. 1202-1210 // DOI: DOI 10.1002/mrm.10171; 2002.

* cited by examiner

MULTI-CONTRAST MRI IMAGE RECONSTRUCTION USING MACHINE LEARNING

CROSS REFERENCE TO RELATED APPLICATIONS

This patent application claims priority to, and the benefit of, U.S. Provisional Patent Application No. 62/979,853, filed Feb. 21, 2020, which is incorporated herein by reference in its entirety.

BACKGROUND

Field

Various examples of the disclosure generally relate to magnetic resonance imaging (MRI). Various examples specifically relate to machine-learned (ML) algorithms used for multi-contrast MRI image reconstruction.

Related Art

Clinical MRI examinations usually consist of multiple MRI scans, showing similar anatomical structures, but fundamentally different contrasts and hence provide complementary diagnostic information. However, the acquisition of multiple contrasts results in long scan times, which limits patient throughput and increases the risk of involuntary patient motion.

In order to limit the duration of the individual scans and reduce motion sensitivity, conventional MRI protocols often rely on thick-slice imaging (4-5 mm) as well as slice gaps (20-30%), which result in loss of information and partial-volume artifacts. Such techniques also lead to the need for redundant acquisitions at multiple imaging orientations to allow for multi-planar viewing. Furthermore, MRI scan time is often further reduced by reducing the spatial resolution along the phase-or partition-encoding directions and applying partial-Fourier techniques, often at the cost of smoothing and ringing artifacts.

Various Parallel Imaging (PI) and iterative reconstruction techniques apply only moderate parallel imaging acceleration (R=2-4) to avoid large image artifacts, g-factor noise amplification and image blurring.

Various acquisition/reconstruction techniques, for example Controlled Aliasing in Parallel Imaging Results in Higher Acceleration (CAIPIRINHA), Bunch-Phase-Encoding, or Wave-CAIPI (Controlled Aliasing in Parallel Imaging) techniques, efficiently mitigate encoding related noise amplification and parallel imaging artifacts, but are prone to noise due to the inherent sqrt(R) signal-to-noise (SNR) penalty caused by the acceleration.

For multi-contrast MRI, more complicated sparsity constraints were proposed to improve image reconstruction. However, fine-tuning of regularization parameters to avoid increased image blurring, over-smoothing as well as unnatural image appearance, requires high computational cost leading to long reconstruction times, which poses a challenge for clinical translation.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 1 schematically illustrates a MRI system according to aspects of the disclosure.

FIG. 2 schematically illustrates a MRI reconstruction method according to aspects of the disclosure.

Figure 5:
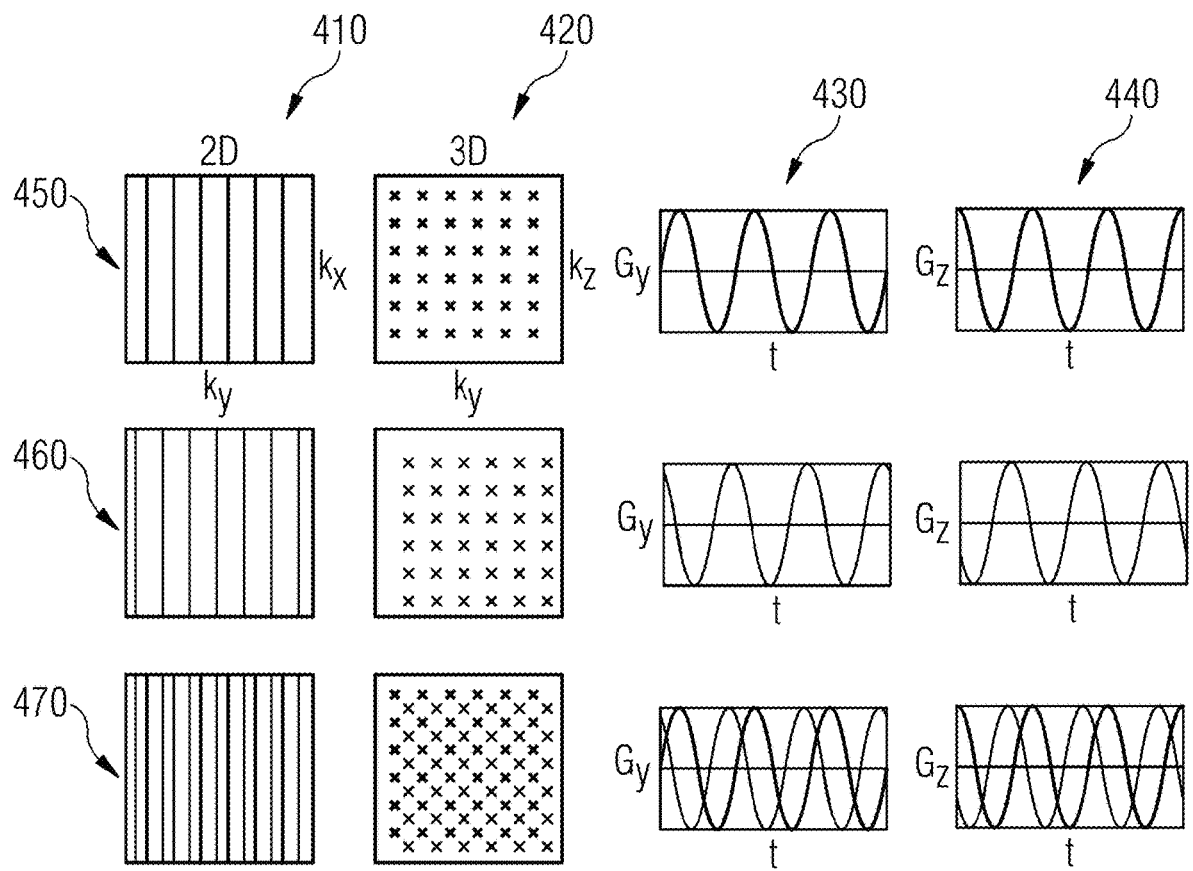

FIG. 5 schematically illustrates varying under-sampling schemes of MRI protocols according to aspects of the disclosure.

Figure 6:
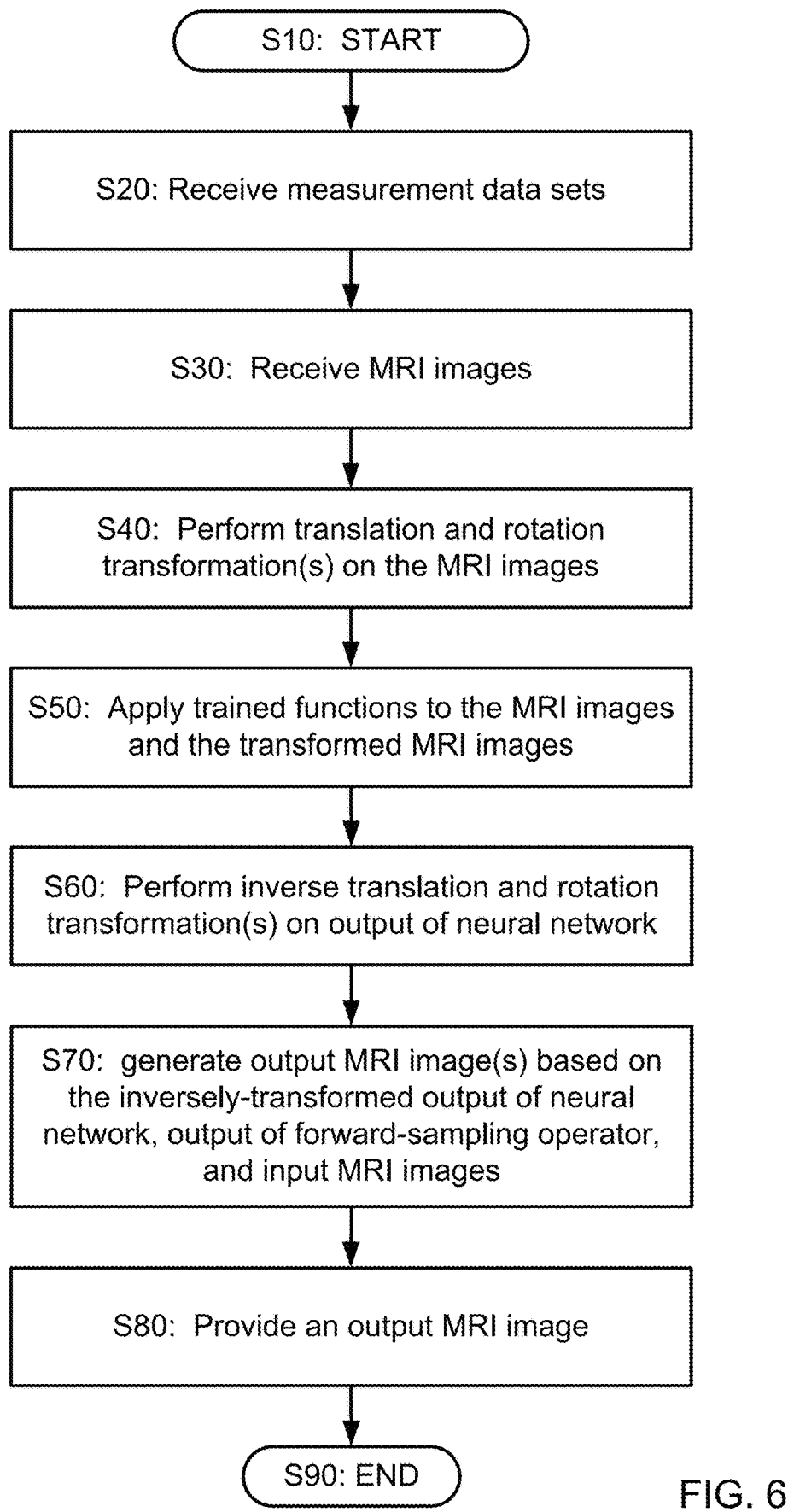

FIG. 6 illustrates a flow chart of a method for reconstructing a MRI image according to aspects of the disclosure.

Figure 7:
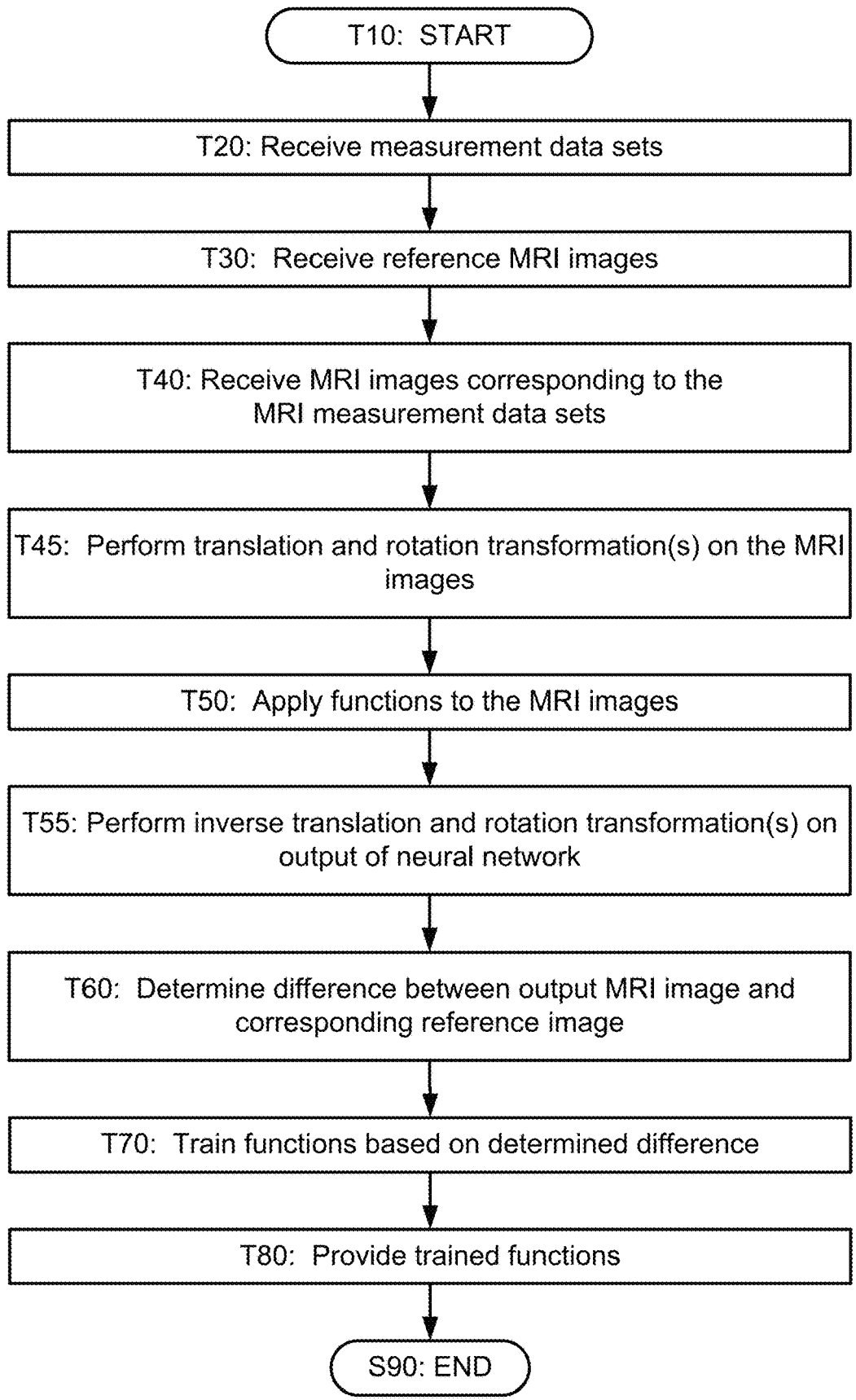

FIG. 7 illustrates a flow chart of a method for providing trained functions for reconstructing an MRI image according to aspects of the disclosure.

Figure 8:
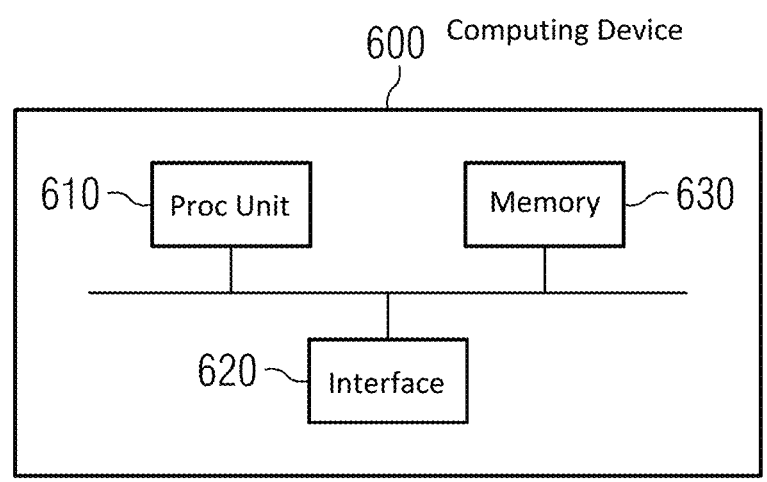

FIG. 8 illustrates a schematic drawing of a device according to aspects of the disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

Aspects of the disclosure include methods and systems for reconstructing a MRI image as well as with respect to methods and systems for providing trained functions for reconstructing an MRI image. Features, advantages, or alternative aspects herein may be assigned to the other aspects and vice versa. In other words, methods and systems according to exemplary embodiments for providing trained functions for reconstructing an MRI image may be improved with features described in context of the methods and systems for reconstructing a MRI image, and vice versa.

In particular, the trained functions, or in other words, trained machine learning functions or algorithms, of the methods and systems for reconstructing a MRI image may be adapted by features of the methods and systems for providing trained functions for reconstructing an MRI image. Furthermore, the MRI input images may comprise advantageous features and aspects of the MRI input training data, and vice versa. Furthermore, the MRI output images may comprise advantageous features and aspects of the MRI output training data, and vice versa.

According to an embodiment, a computer-implemented method for reconstructing a MRI image is provided, comprising the following steps.

In a first step, a plurality of MRI measurement data sets $f_1$ to $f_N$ are received, wherein each MRI measurement data set is acquired from an examination object based on a different MRI protocol of a MRI system.

In general, the MRI measurement data sets may comprise MRI measurement signals acquired from an examination object in an MRI system, which are acquired using radiation of excitation RF pulses and switching of magnetic field gradients, and which are used for reconstructing an MRI image, as known to a person skilled in the art. For example, each of the MRI measurement data sets may comprise MRI image data, and may be based on a specific MRI measurement protocol.

In general, receiving the MRI measurement data sets, and receiving MRI images, may comprise receiving stored MRI measurement data sets or images from an internal or external memory or data storage, and/or transmitting the MRI measurement data sets or images from a MRI system or a computing device. Generally, any known way of transmitting or receiving the MRI measurement data sets may be implemented. The MRI measurement data sets may be acquired from the same examination object, specifically with the same MRI measurement arrangement of the examination object and the MRI system, more specifically the same image angle or viewing angle, and/or from the same MRI system. MRI measurement data sets may correspond to each other, in such a way that only, or substantially only, the MRI measurement protocols, which each MRI measurement data set has been acquired, may be different from each other, whereas other parameters such as for example position of the examining object in the MRI system are the same. Accordingly, MRI measurement data sets $f_1$ to $f_N$ may be in the frequency domain, and may include varying distortions such as noise or artefacts.

In another step, MRI images $u_1^0$ to $u_N^0$ are received, which correspond to the MRI measurement data sets $f_1$ to $f_N$. In particular, each MRI image may correspond to a different MRI measurement data set, i.e. may be an MRI image reconstructed based on the respective MRI measurement data set. In various embodiments, the method may comprise reconstructing the MRI images $u_1^0$ to $u_N^0$ from the MRI measurement data sets $f_1$ to $f_N$, instead of receiving the MRI images.

In general, MRI images $u_1^0$ to $u_N^0$ may be reconstructed images each from a respective MRI measurement data set $f_1$ to $f_N$ according to MRI techniques as known in the art, specifically each MRI image may be reconstructed from one respective MRI measurement data set $f_1$ to $f_N$ based on a specific MRI protocol. Accordingly, MRI images $u_1^0$ to $u_N^0$ may be reconstructed MRI images in the image domain. MRI images $u_1^0$ to $u_N^0$ represent initial reconstructions from the MRI datasets, and accordingly may comprise distortions such as MRI image artefacts based on distortions of the underlying MRI measurement data sets.

In another step, trained functions are applied to the MRI images $u_1^0$ to $u_N^0$ using a neural network and a forward-sampling operator, wherein at least one output MRI image $u^T$ is generated. The trained functions are applied to the MRI images $u_1^0$ to $u_N^0$ in at least a first step $GD^1$.

In general, the step of applying trained functions to the MRI images $u_1^0$ to $u_N^0$ may be performed by an unrolled reconstruction network. The unrolled network may include both the forward sampling operator and the application of trained functions. In an exemplary embodiment, the unrolled network is a variational network, but is not limited thereto.

Applying trained functions to the MRI images $u_1^0$ to $u_N^0$ in at least a first step $GD^1$ may also comprise applying trained functions in a plurality of steps GD in series, including a first step $GD^1$. In step $GD^1$ trained functions are applied to MRI images $u_1^0$ to $u_N^0$, and in further steps $GD^t$ trained functions may be applied to further MRI images $u_1^{t-1}$ to $u_N^{t-1}$, which, wherein in output images $GD^t$ are generated. Therein, the number T of steps GD may be any positive number $T=1 \ldots \infty$, in particular a predetermined number T. As a general rule, the output of a previous step $GD^t$ may be the input for the following step $GD^{t+1}$, in particular an output MRI image $u^t$ of a previous step $GD^t$ may be an input MRI image $u^{t+1}$ of a following step $GD^{t+1}$, for $i=1 \ldots T-1$.

In general, the neural network may comprise a plurality of trained filter functions, using trained filter parameters, wherein, in a step GD each trained filter function in the neural network is applied to each MRI image $u_1^0$ to $u_N^0$ simultaneously, using convolutions and non-linear activations, to provide an output of the neural network, and the forward-sampling operator is applied to each MRI image $u_1^0$ to $u_N^0$ individually to provide an output of the forward-sampling operator. Further, the outputs of the neural network and of the forward-sampling operator may be used to generate the at least one output MRI image $u^T$.

In an exemplary embodiment, translation and rotation transformations are performed before and after the filter operations of the network (i.e. before the convolutions and non-linear activations). These transformations advantageously allow for joint multi-contrast reconstructions in the presence of inter-scan motion. In an exemplary embodiment, before being provided to the neural network, one or more translation and rotation (TR) transformations are performed on the input MRI images $u_1^0$ to $u_N^0$ to co-register the jointly reconstructed scans before the convolutional filtering. The transformed MRI images $u_1^0$ to $u_N^0$ are then subjected to the functions (e.g. convolution filtering and non-linear activations) of the neural network. In an exemplary embodiment, the output of the neural network may be subjected to an inverse-transformation, and the inversely-transformed output and an output of the forward-sampling operator is subtracted from the respective input MRI image $u_1^0$ to $u_N^0$ to generate at least one output MRI image $u^T$.

In an exemplary embodiment, inter-scan motion parameters are computed or otherwise determined by registering the initial parallel imaging reconstructions and utilizing this information when applying the network.

In general, in the neural network only MRI images may be used as an input from an MRI measurement, wherein MRI measurement data sets $f_1$ to $f_N$ and/or coil sensitivities C and/or undersampling schemes of the MRI protocols may not be used and/or may not be an input to the neural network, or in general the variational network, or in the step of applying trained filter functions to the MRI images.

In each step $GD^t$, the forward-sampling operator determines an agreement between at least one MRI image $u_1^0$ to $u_N^0$ and the corresponding MRI measurement data set $f_1$ to $f_N$. In various embodiments, the forward-sampling operator may determine an agreement between each current MRI image $u_1^{t-1}$ to $u_N^{t-1}$ and the corresponding MRI measurement data set $f_1$ to $f_N$ individually. In various embodiments, the forward-sampling operator may determine a difference between at least one MRI image $u_1^0$ to $u_N^0$ and the corresponding MRI measurement data set $f_1$ to $f_N$.

In another step, the at least one output MRI image $u^T$ is provided.

Thereby, an improved method for reconstructing a MRI image is provided, which has improved image quality and reconstruction time for acquisitions with low signal-to-noise (SNR) ratio, where large over-smoothing and unnatural image appearance may be prevented in contrast to a conventional single-contrast method. High robustness towards low SNR is particularly useful for the implementation on clinical 1.5 T scanners, which have inherently lower SNR than 3 T systems. Further, jointly reconstructing multiple MRI protocols using an ML algorithm, enables the network to better differentiate structural aliasing, which appears slightly different in each scan, from anatomical structures. This was found to effectively prevent blurring/ over-smoothing and resulted in much improved image quality.

According to an embodiment, a computer-implemented method for providing trained functions for reconstructing an MRI image is provided, comprising the following steps.

In a step, a plurality of MRI measurement data sets $f_1$ to $f_N$ are received, wherein each data set is acquired from an examination object based on a different MRI protocol of a MRI system.

In another step, reference MRI images $g_1$ to $g_N$ are received, which are images with reduced MRI artefacts and/or noise amplification compared to the MRI images $u_1^0$ to $u_N^0$, each reference MRI images $g_1$ to $g_N$ corresponding to a respective one of MRI measurement data sets $f_1$ to $f_N$, respectively to the examination object and the MRI system underlying MRI protocol.

In general, reference MRI images $g_1$ to $g_N$ may also be referred to as ground truth images $g_1$ to $g_N$ for each MRI protocol, as known in the field of machine learning. Reference MRI images $g_1$ to $g_N$ may represent the desired outcome of a machine learning algorithm, in particular they may be MRI pictures with ideally no image artefacts and distortions, and they may be MRI images with reduced MRI artefacts and/or noise amplification compared to the MRI images $u_1^0$ to $u_N^0$. As such, they may be used as reference MRI images to compare the output MRI images of the machine learning algorithms with, in order to determine the quality of the output MRI images. In various embodiments, the reference MRI images $g_1$ to $g_N$ may be MRI images, which have been reconstructed based on MRI image data, which is based on a respective MRI system setup with a higher resolution, i.e. longer measurement time, and/or in various embodiments, which is fully sampled in k-space. A ML algorithm may include one or more parameters that are trained based on at least one of ground truth images $g_1$ to $g_N$, or on the plurality of ground truth images $g_1$ to $g_N$.

In another step, MRI images $u_1^0$ to $u_N^0$ are received, which correspond to the MRI measurement data sets $f_1$ to $f_N$, wherein each MRI measurement data set is based on a corresponding MRI image $u_1^0$ to $u_N^0$.

In a further step, functions are applied to the MRI images $u_1^0$ to $u_N^0$ using a neural network and a forward-sampling operator. Functions may be applied to the MRI images $u_1^0$ to $u_N^0$ in at in at least a first step $GD^1$, or in a number T of steps $GD^1$ to $GD^T$.

Applying the functions to the MRI images u may be performed by the same variational network as described for the method for reconstructing a MRI image.

The forward-sampling operator determines an agreement between at least one MRI image $u_1^0$ to $u_N^0$ and the corresponding MRI measurement data set $f_1$ to $f_N$. Therein, at least one output MRI image $u^T$ is generated.

In a next step, a difference between the at least one output MRI image $u^T$ and the corresponding reference image $g_i$ is determined. The at least one output MRI image $u^T$ and the corresponding reference image g may be based on the same MRI protocol.

In a further step, the functions are trained based on the determined difference, and in another step, the trained functions are provided, which can, then, be applied to a further set of MRI images based on the same MRI protocols, but showing a different examination object.

According to an embodiment, a computing device is provided, which is configured for reconstructing an MRI image, the computing device comprising a memory, an interface, and at least one processing unit, the memory containing instructions executable by said at least one processing unit, wherein execution of the instructions causes the computing device to execute the following steps.

In a first step, a plurality of MRI measurement data sets $f_1$ to $f_N$ is received by the interface, wherein each data set is acquired from an examination object based on a different MRI protocol.

In another step, MRI images $u_1^0$ to $u_N^0$ are reconstructed by the processing unit, from the MRI measurement data sets $f_1$ to $f_N$.

In a next step, trained functions are applied to the MRI images $u_1^0$ to $u_N^0$, using a neural network and a forward-sampling operator, wherein at least one output MRI image $u_i^T$ is generated. The trained functions are applied to the MRI images $u_1^0$ to $u_N^0$ in at least a first step $GD^1$, for example, the trained functions may be applied in a number T of steps $GD^1$ to $GD^T$, as described for various embodiments. Therein, the forward-sampling operator determines an agreement between at least one MRI image $u_1^0$ to $u_N^0$ and the corresponding MRI measurement data set $f_1$ to $f_N$.

In a further step, the at least one output MRI image $u^T$ is provided by the interface.

The computing device for reconstructing an MRI image may be further configured to perform any other method or combination of methods according to the disclosure.

According to an embodiment, a MRI system is provided, which is configured or operative for performing any method for reconstructing a MRI image or providing trained functions for reconstructing an MRI image according to the disclosure.

According to an embodiment, a computer program product is provided, which comprises program code to be executed by at least one processor of a computing device. Therein, the execution of the program code causes the at least one processor to execute one of the methods for reconstructing a MRI image or providing trained functions for reconstructing an MRI image according to the disclosure.

According to an embodiment, a computer-readable storage medium is provided, comprising instructions which, when executed by a computer, cause the computer to carry out one of the methods for reconstructing a MRI image or providing trained functions for reconstructing an MRI image according to the disclosure.

For such a computing device, MRI system, computer program product, and computer-readable storage medium for reconstructing a MRI image and for providing trained functions for reconstructing an MRI image, technical effects may be achieved, which correspond to the technical effects described for the methods for reconstructing a MRI image and providing trained functions for reconstructing an MRI image.

Although specific features described in the disclosure are described in connection with specific examples or embodiments, it is to be understood that the features may not only be used in the respective combinations, but may also be used isolated, and features from different examples or embodiments may be combined with each other, and correlate to each other, unless specifically noted otherwise.

Clinical MRI examinations usually consist of multiple MRI scans, showing similar anatomical structures, but fundamentally different contrasts and hence provide complementary diagnostic information. However, the acquisition of multiple contrasts results in long scan times, which limits patient throughput and increases the risk of involuntary patient motion.

To limit the duration of each individual scan and reduce motion sensitivity, conventional MRI protocols often rely on thick-slice imaging (4-5 mm) as well as slice gaps (20-30%) which result in loss of information and partial-volume artifacts. Such approaches also lead to the need for redundant acquisitions at multiple imaging orientations to allow for multi-planar viewing. Furthermore, MRI scan time is often further cut by reducing the spatial resolution along the phase- or partition-encoding directions and applying partial-Fourier techniques, often at the cost of smoothing and ringing artifacts.

Over the last decade, several parallel imaging (PI) and iterative reconstruction techniques were proposed to accelerate MRI acquisitions. Nonetheless, to avoid large image artifacts, g-factor noise amplification and image blurring/smoothing most clinical protocols apply only moderate parallel imaging acceleration (R=2-4).

Parallel imaging (PI) techniques such as GRAPPA, as disclosed in the document Griswold, Mark A., et al. "Generalized autocalibrating partially parallel acquisitions (GRAPPA)." Magnetic Resonance in Medicine: An Official Journal of the International Society for Magnetic Resonance in Medicine 47.6 (2002): 1202-1210, and SENSE, as disclosed in the document Pruessmann, Klaas P., et al. "SENSE: sensitivity encoding for fast MRI." Magnetic resonance in medicine 42.5 (1999): 952-962, accelerate MRI acquisitions by taking advantage of the inherent image encoding information of modern multi-channel receiver arrays. Nonetheless, these techniques are limited to low parallel imaging acceleration (R=2 or 3) to prevent image artifacts and large g-factor noise penalties.

More advanced acquisition/reconstruction techniques, such as CAIPIRINHA, as disclosed in the document Breuer, Felix A. et al. "Controlled aliasing in volumetric parallel imaging (2D CAIPIRINHA)." Magnetic Resonance in Medicine: An Official Journal of the International Society for Magnetic Resonance in Medicine 55.3 (2006): 549-556, Bunch-Phase-Encoding, as disclosed in the document Moriguchi, Hisamoto, and Jeffrey L. Duerk. "Bunched phase encoding (BPE): a new fast data acquisition method in MRI." Magnetic Resonance in Medicine: An Official Journal of the International Society for Magnetic Resonance in Medicine 55.3 (2006): 633-648, or Wave-CAIPI, as disclosed in the document Bilgic, Berkin, et al. "Wave-CAIPI for highly accelerated 3D imaging." Magnetic resonance in medicine 73.6 (2015): 2152-2162, were proposed to better exploit variations in the coil sensitivity profile and were shown to enable up to an order of magnitude acceleration both for SMS, as disclosed in the document Gagoski, Borjan A., et al. "RARE/turbo spin echo imaging with simultaneous multislice Wave-CAIPI." Magnetic resonance in medicine 73.3 (2015): 929-938, and 3D imaging sequences, as disclosed in the document Bilgic, Berkin, et al. "Wave-CAIPI for highly accelerated 3D imaging." Magnetic resonance in medicine 73.6 (2015): 2152-2162, the document Polak, Daniel, et al. "Wave-CAIPI for highly accelerated MP-RAGE imaging." Magnetic resonance in medicine 79.1 (2018): 401-406, and the document Polak, Daniel, et al. "Highly-accelerated volumetric brain examination using optimized wave-CAIPI encoding." Journal of Magnetic Resonance Imaging (2019).

Various acquisition/reconstruction techniques, in particular CAIPIRINHA, Bunch-Phase-Encoding, or Wave-CAIPI techniques, efficiently mitigate encoding related noise amplification and parallel imaging artifacts, however, despite negligible g-factor and almost no artifacts, they are prone to noise due to the inherent sqrt(R) signal-to-noise (SNR) penalty caused by the acceleration.

Iterative reconstruction techniques, such as Total Variation (TV), Compressed Sensing (CS) or combined PI-CS approaches, as disclosed in the document Lustig, Michael, David Donoho, and John M. Pauly. "Sparse MRI: The application of compressed sensing for rapid MR imaging." Magnetic Resonance in Medicine: An Official Journal of the International Society for Magnetic Resonance in Medicine 58.6 (2007): 1182-1195, enable higher acceleration while mitigating large noise and artifact penalties.

Specifically for multi-contrast imaging, more complicated sparsity constraints were proposed to improve the image reconstruction, as disclosed in the document Bilgic, Berkin, Vivek K. Goyal, and Elfar Adalsteinsson. "Multi-contrast reconstruction with Bayesian compressed sensing." Magnetic resonance in medicine 66.6 (2011): 1601-1615, the document Gong, Enhao, et al. "PROMISE: Parallel-imaging and compressed-sensing reconstruction of multicontrast imaging using SharablE information." Magnetic resonance in medicine 73.2 (2015): 523-535, and the document B. Bilgic, S. Cauley, L. Wald, and K. Setsompop, "Joint SENSE reconstruction for faster multi-contrast wave encoding," in Proc. Intl. Soc. Mag. Res. Med., 2018, p. 0940.

However, the quality of these techniques largely depends on the type of acquisition—3D and dynamic imaging sequences provide more sparsity than 2D acquisitions and generally lead to better results. Fine-tuning of the regularization parameters is important to avoid increased image blurring, over-smoothing as well as unnatural image appearance. Ultimately, the high computational cost of these methods leads to long reconstruction times, which poses a challenge for clinical translation.

Recently, the application of Deep Learning (DL) for the task of image reconstruction found wide spread attention in the MRI research community. As disclosed in the document Hammernik, Kerstin, et al. "Learning a variational network for reconstruction of accelerated MRI data." Magnetic resonance in medicine 79.6 (2018): 3055-3071, and the document Cheng, Joseph Y., et al. "Highly Scalable Image Reconstruction using Deep Neural Networks with Bandpass Filtering." arXiv preprint arXiv:1805.03300 (2018), these methods provide improved image quality for the reconstruction of highly under-sampled datasets when compared to conventional approaches without DL.

The advantage of these techniques is that patient-specific tuning of the regularization parameters is not required and the reconstruction time is usually several orders of magnitude faster than most iterative methods. Reconstructing multiple contrasts jointly was demonstrated in document Gong, E., G. Zaharchuk, and J. Pauly. "Improving the PI+CS reconstruction for highly undersampled multi-contrast MRI using local deep network." Proceedings of the 25th Annual Meeting of the ISMRM, Honolulu, HI. 2017.

Hereinafter, techniques of Magnetic Resonance Imaging (MRI) are described. MRI may be employed to obtain raw MRI measurement data of a magnetization of nuclear spins of a sample region of an examination object, or a patient. The sample region defines a field of view. The MRI measurement data is typically defined in k-space. Based on the MRI measurement data sets, MRI images in image domain may be determined.

According to various embodiments, the MRI measurement data may be obtained using an under-sampling scheme. When acquiring MRI measurement data using an under-sampling scheme, for certain k-space locations, raw data samples are not acquired and the missing information is reconstructed later on. A so-called acceleration factor R is indicative of the fraction of those k-space locations along a k-space trajectory associated with the under-sampling scheme for which no raw data samples are acquired. Larger (smaller) acceleration factors may result in a shorter (longer) scan times. For reconstruction of the missing information, respectively for determining a reconstructed MRI dataset, often a predetermined or calibrated sensitivity profile of multiple receiver coils of the RF receiver of the MRI device is used. Thereby, aliasing effects resulting from the under-sampling may be reduced to some extent. An analytic algorithm may be employed. Such techniques are sometimes referred to as parallel acquisition techniques (PATs).

For example, the GRAPPA PAT linearly combines the undersampled MRI measurement data in k-space to estimate the missing samples in k-space; parameters of the combination are determined using auto-calibration signals (ACS) sampled with Nyquist rate, e.g., at k-space center. A respective kernel is defined.

The methods according to exemplary embodiments of the disclosure may be referred to as Machine Learning (ML)/Deep Learning mechanisms, or algorithms. According to exemplary embodiments, the reconstruction of an MRI dataset is facilitated using an ML algorithm, and/or using trained functions. The ML algorithm may be applied to an initial MRI dataset, which may comprise or consist of a plurality of MRI images. The initial MRI dataset may be reconstructed from undersampled MRI measurement data using a PAT, e.g., GRAPPA or CAIPIRINHA. Then, the ML algorithm may refine the reconstruction of the initial MRI dataset.

As a general rule, the ML algorithm employed in the various embodiments may include a trained neural network, e.g., a deep-learning network, or variational network. The ML algorithm may include a variational model. The variational model may include (i) a regularization operator, such as a Convolutional Neural Network (CNN), for filtering of the input MRI dataset using convolutions 213 and non-linear activations 214 (see also FIG. 2); and (ii) a forward-sampling operator (sometimes also referred to as data-consistency operator, or data fidelity operator) for computation of an MRI forward model to assure agreement of the reconstructed MRI dataset with the MRI measurement data.

The ML algorithm may include multiple iterations of (i) and (ii), to iteratively refine the reconstructed MRI dataset, wherein an appropriate optimization technique, for example a gradient descent optimization technique as known in the art, may be used to optimize parameters used in the trained functions, i.e. in the steps and/or filters, in other words to train the convolutional filter kernels (213) and non-linear activations (214).

By using the ML algorithm (e.g., by using a training to determine parameters of a variational model), an increased image quality of the respective reconstructed MRI dataset may be provided. A reduced noise amplification and reduced image artefacts in comparison with the conventional parallel imaging or constrained reconstructions. The natural image appearance may be better preserved using ML algorithm, e.g., without causing significant blurring in comparison to techniques with hand-crafted regularization operators. Conventional compressed sensing techniques may be slow and may result in less natural looking images. Using the ML algorithm, faster image reconstruction may be achieved using a predefined number of iterations of the ML algorithm.

One or more parameters of the ML algorithm may be determined using a training based on a ground-truth MRI dataset, which may comprise reference MRI images with reduced MRI artefacts and/or noise amplification, before the reconstruction may be executed to provide a reconstructed MRI dataset. An offline end-to-end training is possible to obtain better results.

In general, a trained function mimics cognitive functions that humans associate with other human minds. In particular, by training based on training data the trained function is able to adapt to new circumstances and to detect and extrapolate patterns.

In general, parameters of a trained function may be adapted by means of training. In particular, supervised training, semi-supervised training, unsupervised training, reinforcement learning and/or active learning may be used. Furthermore, representation learning (an alternative term is "feature learning") may be used. In particular, the parameters of the trained functions may be adapted iteratively by several steps of training.

In particular, a trained function may comprise a neural network, a support vector machine, a decision tree and/or a Bayesian network, and/or the trained function may be based on k-means clustering, Q-learning, genetic algorithms and/or association rules. In particular, a neural network may be a deep neural network, a convolutional neural network or a convolutional deep neural network. Furthermore, a neural network may be an adversarial network, a deep adversarial network and/or a generative adversarial network.

Figure 1:
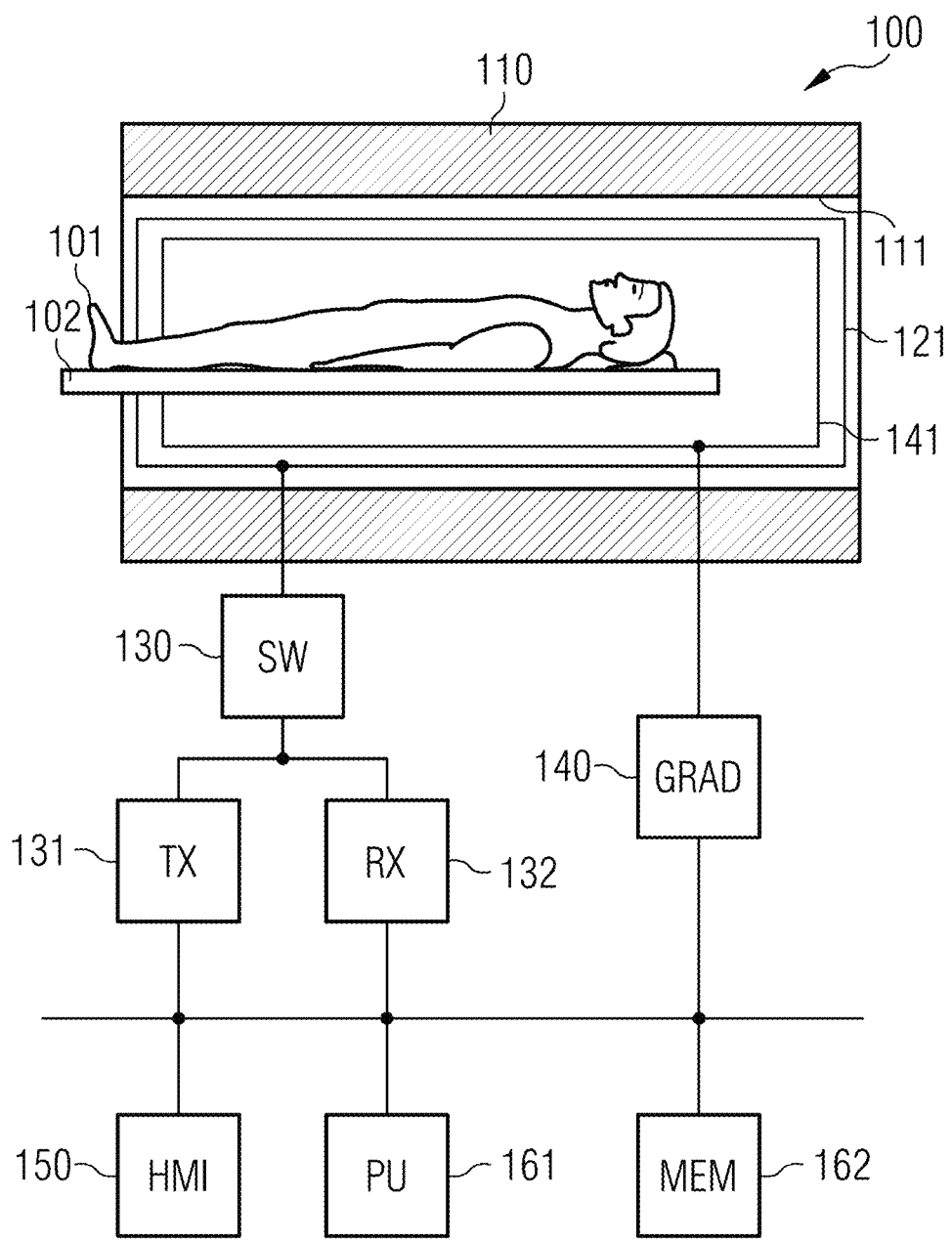

FIG. 1 schematically illustrates a MRI device 100, according to aspects of the disclosure.

In an exemplary embodiment, the MRI device 100 includes a magnet 110 which defines a bore 111. The magnet 110 may provide a DC magnetic field of one to six Tesla along its longitudinal axis. The DC magnetic field may align the magnetization of the patient 101 along the longitudinal axis. The patient 101 may be moved into the bore by means of a movable table 102.

The MRI device 100 also includes a gradient system 140 for creating spatially-varying magnetic gradient fields (gradients) used for spatially encoding MRI data. Typically, the gradient system 140 includes at least three gradient coils 141 that are arranged orthogonal to each other and may be controlled individually. By applying gradient pulses to the gradient coils 141, it is possible to apply gradients along certain directions. The gradients may be used for slice selection (slice-selection gradients), frequency encoding (readout gradients), and phase encoding along one or more phase-encoding directions (phase-encoding gradients). Hereinafter, the slice-selection direction will be defined as being aligned along the Z-axis; the readout direction will be defined as being aligned with the X-axis; and a first phase-encoding direction as being aligned with the Y-axis. A second phase-encoding direction may be aligned with the Z-axis. The directions along which the various gradients are applied are not necessarily in parallel with the axes defined by the coils 141. Rather, it is possible that these directions are defined by a certain k-space trajectory, which, in turn, may be defined by certain requirements of the respective MRI sequence and/or based on anatomic properties of the patient 101.

For preparation and/or excitation of the magnetization polarized/aligned with the DC magnetic field, RF pulses may be applied. For this, an RF coil assembly 121 is provided which is capable of applying an RF pulse such as an inversion pulse or an excitation pulse. While the inversion pulse generally inverts the direction of the longitudinal magnetization, excitation pulses may create transversal magnetization.

For creating such RF pulses, a RF transmitter 131 is connected via a RF switch 130 with the coil assembly 121. Via a RF receiver 132, it is possible to detect signals of the magnetization relaxing back into the relaxation position aligned with the DC magnetic field. In particular, it is possible to detect echoes; echoes may be formed by applying one or more RF pulses (spin echo) and/or by applying one or more gradients (gradient echo). The magnetization may inductively coupled with the coil assembly 121 for this purpose. The respectively acquired MRI measurement data may correspond to raw data in k-space; according to various embodiments, the MRI measurement data may be post-processed in order to obtain images. Such post-processing may include a Fourier Transform from k-space to image space. Such post-processing may also include reconstruction to avoid aliasing where an under-sampling scheme is used.

Generally, it would be possible to use separate coil assemblies for applying RF pulses as well as for acquiring MRI data (not shown in FIG. 1). For example, for applying RF pulses a comparably large body coil 121 may be used; while for acquiring MRI data a surface coil assembly including an array of comparably small coils could be used. For example, the surface coil assembly could include 32 individual RF coils and thereby facilitate PATs relying on spatially-offset coil sensitivities.

The MRI device 100 further includes a human machine interface 150, e.g., a screen, a keyboard, a mouse, computer, tablet, etc. By means of the human machine interface 150, a user input may be detected and output to the user may be implemented. For example, by means of the human machine interface 150, it is possible to set certain configuration parameters for the MRI sequences to be applied.

The MRI device 100 further includes a processing unit (PU) 161. The processing unit 161 may include one or more processors, such as one or more graphics processing units (GPUs) and/or one or more central processing units (CPUs). The processing unit 161 may implement various control functionality with respect to the operation of the MRI device 100, e.g., based on program code loaded from a memory 162. For example, the processing unit 161 could implement a sequence control for time-synchronized operation of the gradient system 140, the RF transmitter 131, and the RF receiver 132. The processing unit 161 may also be configured to implement a reconstruction procedure, i.e., implement post-processing for reconstruction of an MRI dataset based on MRI measurement data. For example, the processing unit 161 could be configured to apply a PAT to obtain a reconstructed, initial MRI dataset and to apply a ML algorithm to obtain, based on the initial MRI dataset, a (refined) reconstructed MRI dataset. Details with a procedures that may be executed by the processing unit 161 based on program code loaded from the memory 162 will be illustrated in connection with FIG. 2. The processing unit 161 may be a controller in one or more embodiments. In an exemplary embodiment, the processing unit 161 includes processor circuitry that is configured to perform one or more functions and/or operations of the processing unit 161.

Detailed descriptions of MRI acquisition, data pre-processing and DL reconstruction techniques in accordance with aspects and aspects of the disclosure will be explained.

Figure 2:
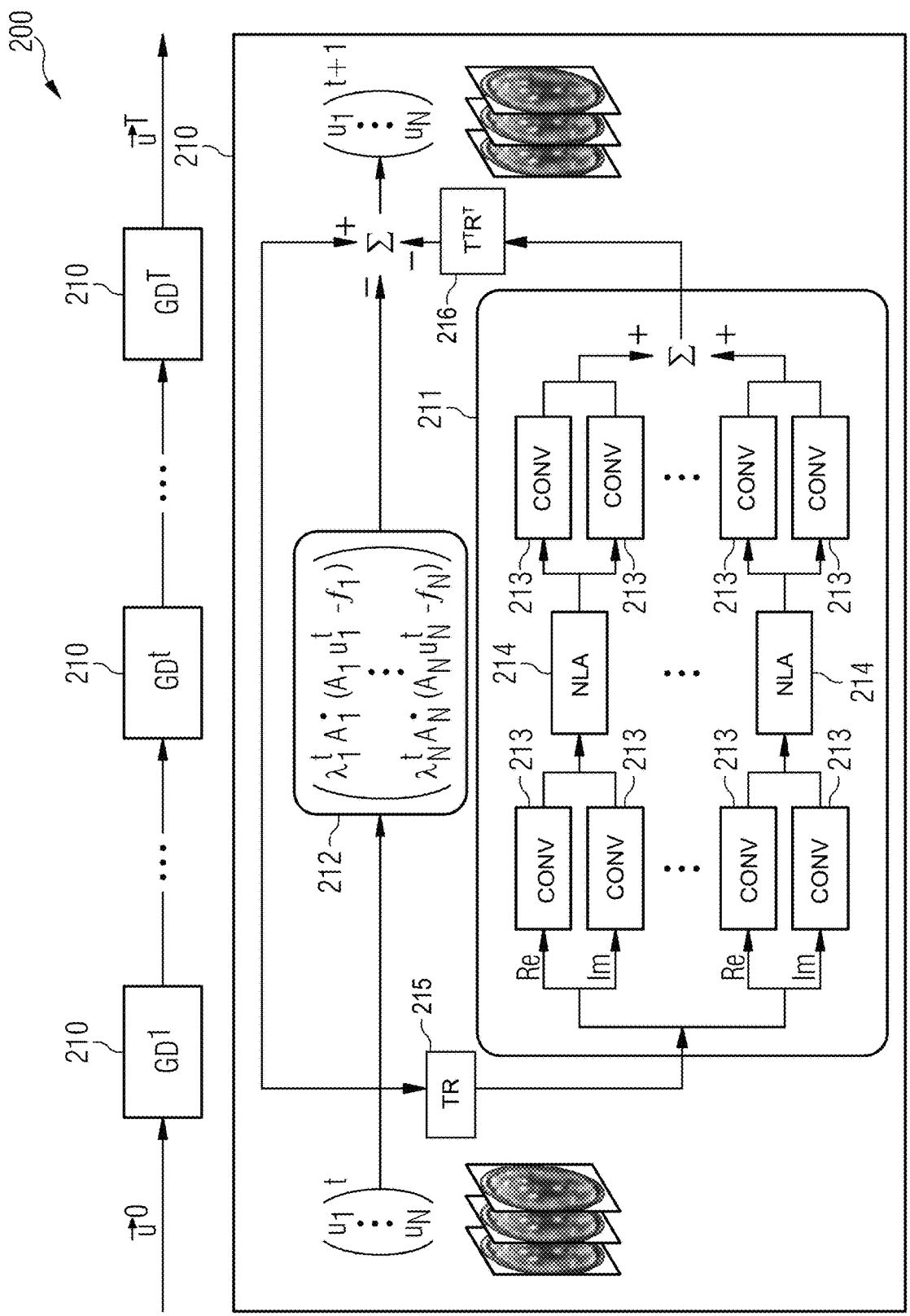

FIG. 2 schematically illustrates a MRI reconstruction method according to aspects of the disclosure.

Referring to FIG. 2, the method includes a series of gradient descent steps GD (210), which are performed in a variational network (200).

MRI images $u^0$, comprising a plurality of MRI images $u_1^0$ to $u_N^0$, are provided to a first gradient descent step $GD^1$. The number of steps GD is a predefined number T, such that a plurality of steps $GD^1$ to $GD^T$ is performed in series, wherein the output of a last step $GD^T$ is at least one image $u^T$. In this example the at least one output image $u^T$ comprises a plurality of out MR images $u_1^T$ to $u_N^T$, each based on a respective MRI protocol, or MRI contrast, of a plurality of MRI protocols 1 . . . N.

An exemplary step $GD^t$ (210) for a $t=\{1, \ldots, T\}$ will be described in detail in the following.

The MRI images $u^0$ are initially reconstructed MRI images from a plurality of MRI measurement data sets $f_1$ to $f_N$, where the MRI measurement data sets are acquired from an examination object based on different MRI protocols, in particular different MRI contrasts, of a MRI system. In this example, the MRI images $u_1^0 \ldots N$ are reconstructed from MRI measurement datasets using, for example, aSENSE-based reconstruction technique, or any other conventional reconstruction technique, as known in the art.

In an exemplary embodiment, for the MRI measurement data sets $f_1$ to $f_N$ and corresponding MRI images $u^0$, one or more of the following general aspects apply:

The MRI measurement data sets $f_1$ to $f_N$ may be based on multiple MRI protocols, specifically multiple contrasts, more specifically multiple accelerated contrasts, either 2D or 3D, of the MRI system.

- Additionally, calibration data, either internal or external, may be acquired for at least one of the MRI protocols to compute coil sensitivities C.
- To improve the image quality of the Multi-Contrast (MC) Deep Learning (DL) reconstruction methods, the under-sampling schemes between different MRI protocols may be varied, ideally in a complementary fashion. Complementary in this regard may mean ideally complementary k-space sampling, which may comprise no overlap at all (0%), however complementary may also comprise that overlap between the under-sampling schemes is lower than 50%, particularly 20%, more particularly 10%, and/or wherein the acquired k-space points may be distributed with substantially even distances in k-space. These thresholds have shown to provide more efficient filtering with less image distortions, compared to similar, or same, under-sampling schemes. It is to be noted, that the acceleration factor may be varied between the different MRI protocols, which may reduce the overall scan time.
- If Wave-CAIPI encoding is used, the Wave corkscrew for each contrast may be varied, e.g. by rotating the corkscrew around the kx (readout) axis and/or vary the number of cycles and/or gradient amplitude, and similar variations, as will be explained below with regard to FIG. 5.
- Navigator, motion camera (KinetiCor) or other registration techniques may be utilized, in order to mitigate motion during/between scans.

for at least one MRI contrast, or for each MRI contrast, one or more of the following data pre-processing steps may be applied.

Coil sensitivities, in other words coil sensitivity maps, C may be computed from internal/external calibration data, wherein the computation may only be necessary once. If wave-encoding is used, a Wave Point-Spread-Function (PSF) may be computed.

The under-sampled multi-channel k-space data may be Fourier-transformed along all spatial dimensions to obtain measurement data f, wherein non-acquired samples in k-space may be filled with zeros.

Initial parallel imaging reconstruction using for example SENSE, GRAPPA, Wave-CAIPI or a similar technique, may be performed on under-sampled multi-channel data to create MR images $u^0$ for the DL reconstruction.

A low-resolution background phase may be removed from initial reconstructions $u^0$. It is to be noted, that background phase removal may also be accounted for in coil sensitivity C and measurement data f.

In an exemplary embodiment, the MRI datasets, (i.e. the coil sensitivities C, the PSF, the measurement data f, initial reconstructions $u^0$) and for training methods, the ground truth images g may be divided into patches or patches of collapsing voxel groups, to reduce the computational cost of the DL reconstruction and avoid exceeding GPU memory limitations. Further, if Wave-encoding is used, advantages may also be realized from the sparsity along the readout. Examples of techniques for dividing datasets into patches of collapsing voxel groups are described in U.S. Provisional Application No. 62/799,964, filed Feb. 1, 2019, and U.S. application Ser. No. 16/778,800, filed Jan. 31, 2020, each of which is incorporated herein by reference in its entirety.

According to various embodiments, patches of the above-mentioned MRI datasets may be determined in accordance with a patching scheme that is based on the undersampling schemes.

The patching scheme may define the number, arrangement, overlap, etc. of the patches, wherein a patch, or each patch, may include a subfraction of all voxels of the initial MRI dataset. Each patch includes voxels of multiple sub-regions of the initial MRI dataset, wherein the sub-regions may be offset from each other.

In an exemplary embodiment, for each one of the patches, the ML algorithms are applied to obtain a respective patch of a reconstructed MRI dataset, the machine-learned algorithm depending on the undersampling scheme, and the patches of the reconstructed MRI dataset are combined.

Therein, the size of the sub-regions (and, hence, also their count and the count of voxels per patch) may be predefined. A Size of the sub-regions may be determined depending on a size of the memory 162 available to hold the respective data when applying the ML algorithm.

The sub-regions may be selected in accordance with a undersampling scheme. For example, if a R=3×3 undersampling scheme is used, the overall initial MRI datasets are divided into 3×3 groups of collapsing voxels. Then, each group is divided into a number of sub-regions associated with the respective patch. In other words and more generally, the sub-regions are interleaved in accordance with the acceleration factor of the undersampling scheme.

In some embodiments, it would be possible that there is an overlap defined between the patches. Provisioning the overlap helps to further increase the image quality.

Using Patches for computation enables an efficient computation of the MRI forward model using only pointwise multiplications and summations, wherein time-consuming Fourier transformations along the PE/PAR are not needed.

The initially reconstructed MR images $u_1^0$ to $u_N^0$ of each MRI protocol 1 . . . N, i.e. MRI contrast 1 . . . N, may be stacked along a channel dimension of the DL network to provide MRI images $u^0$.

In exemplary embodiments, MRI images $u_1^0$ to $u_N^0$ may generally be reconstructed each from a respective MRI measurement data set $f_1$ to $f_N$ according to various techniques as known to a person in the art, specifically each MRI image may be reconstructed from one respective MRI measurement data set $f_1$ to $f_N$. Accordingly, MRI images $u_1^0$ to $u_N^0$ may be reconstructed MRI images in the image domain. MRI images $u_1^0$ to $u_N^0$ represent initial reconstructions from the MRI datasets, and accordingly may comprise distortions such as MRI image artefacts based on distortions of the underlying MRI measurement data sets.

With reference to FIG. 2, a multi-contrast (MC) reconstruction procedure may use Deep Learning to jointly reconstruct multiple highly under-sampled MRI contrasts, such as T1w, T2w, T2*w and the like, acquired using complementary k-space under-sampling.

In a variational network architecture, the acquired multi-channel scanner raw data of each contrast and the corresponding under-sampling schemes may be utilized in the reconstruction.

In an exemplary embodiment, deep learning architectures may employ an unrolled gradient descent (GD) network architecture, where the reconstructed images are iteratively refined. Each gradient descent step (GD) in this network contains a (1) Regularization term: learnt filters and non-linear activations; and (2) Data term: traditional MR forward model computation.

Figure 3:
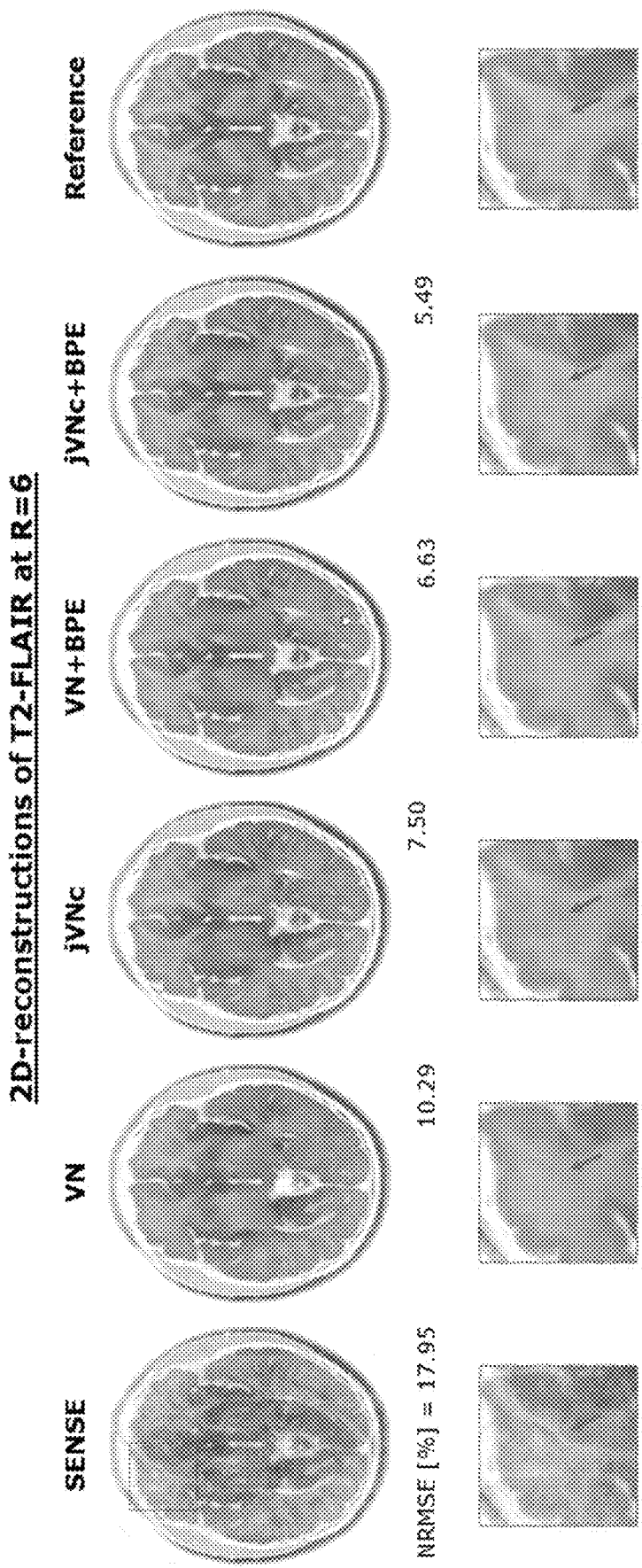
FIG. 3 illustrates various image reconstructions according to aspects of the disclosure.

In an exemplary embodiment, multi-contrast reconstructions expand the network by stacking multiple clinical contrasts along the channel dimension of the network. This allows crosstalk between the jointly reconstructed scans in the regularization term, where non-linear filtering enables the exchange of shared information. As shown in FIG. 3, at R=6-fold acceleration, the SENSE reconstruction of T2-FLAIR resulted in large noise amplification and aliasing artifacts, which were mostly mitigated using the single-contrast variational network (VN). However, by reconstructing T1w, T2w and T2-FLAIR contrasts jointly (jVNc) or utilizing BPE (VN+BPE), fine anatomical details were better preserved and the over-smoothing reduced. The overall best performance was achieved by jVNc+BPE which is also reflected in the lowest NRMSE (computed across 36 slices). This advantageously enables improved differentiation between anatomical structures and aliasing artifacts resulting in better preservation of the spatial resolution and image contrast.

In an exemplary embodiment, for the training of such networks, fully sampled MR data may be acquired for all jointly reconstructed contrasts. Such data can be co-registered channel-by-channel to mitigate any inter-scan motion between the acquisitions of contrasts (e.g. T1w, T2w, T2*w, etc.).

Next, data is retrospectively under sampled and an initial parallel imaging reconstruction is performed which serves as the input to the deep learning network. Corresponding ground truth images are obtained directly from the fully sampled scanner data of each contrast. In the training of the ML network, filter weights are optimized to minimize the difference of the ML output and the ground truth data with respect to a pre-defined error metric.

Figure 4:
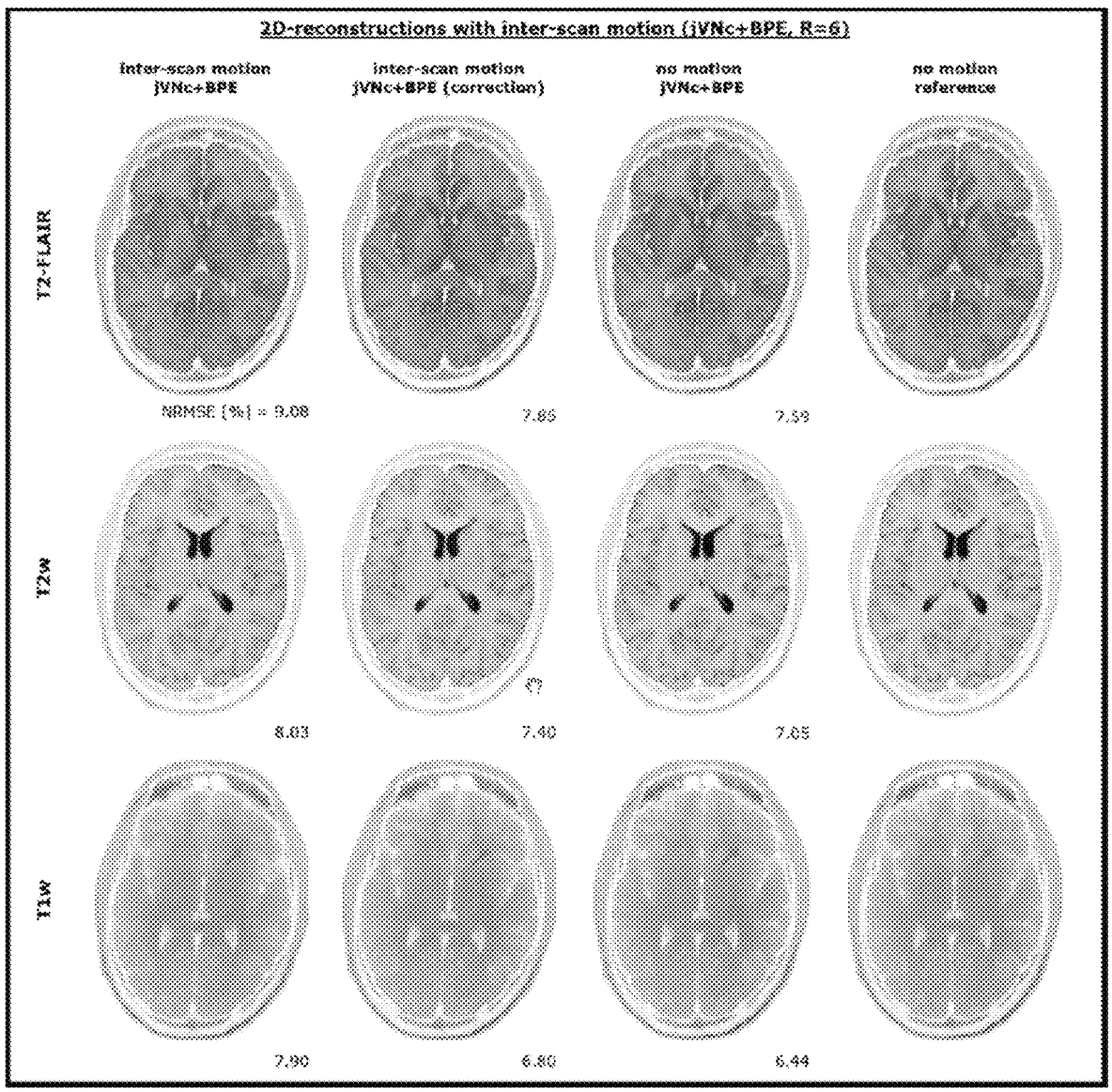
FIG. 4 illustrates various image reconstructions according to aspects of the disclosure.

For the application of the network (inference), typically under-sampled (accelerated) data is passed through the feed-forward path of the network to refine the image quality. However, as illustrated in FIG. 4 in the presence of inter-scan motion between the jointly reconstructed scans, joint multi-contrast reconstructions may result in residual artifacts, as the deep learning network was solely trained on registered data. Also, channel-by-channel co-registration of the accelerated scanner data is not feasible due to under-sampling/aliasing artifacts in accelerated acquisitions. As shown in FIG. 4, inter-scan motion caused artifacts (magenta arrows) in joint multi-contrast reconstructions (jVNc+BPE) have been significantly reduced using the motion mitigation techniques according to exemplary embodiments.

With continued reference to FIG. 2, the employed network architecture includes filtering and MRI forward model computation operations, which are repeated multiple times, in order to iteratively refine the reconstruction. The filtering and computation operations may be performed independently and/or simultaneously of each other, enabling a faster computation.

In the filtering operation, the input MRI image(s)/contrast (s) $u_1^0$ to $u_N^0$ using convolutions 213 and non-linear activations 214 by the neural network 211 simultaneously, where each of the filtering functions is applied to each of MR input images. The convolutional filter (i.e. neural network or convolutional neural network (CNN) may be applied to each complete stack of contrast images (i.e. input MRI images $u_1^{t-1}$ to $u_N^{t-1}$) simultaneously, using/enabling cross-talk between the different images, thereby better differentiation between anatomy and artifacts is provided.

In the computation operation, the MRI forward model is determined to assure agreement with the acquired scanner data, by forward-sampling operator 212 for each input MR image individually.

In an exemplary embodiment, the network architecture (i.e. one or more (e.g. all) of the gradient descent (GD) operations 210) further includes translation and rotation transformations 215, 216. These transformations advantageously allow for joint multi-contrast reconstructions in the presence of inter-scan motion.

In an exemplary embodiment, one or more translation and rotation (TR) transformations 215 are performed on the input MRI image $u_1^0$ to $u_N^0$ before the convolutional filters 213 to co-register the jointly reconstructed scans before the convolutional filtering. The transformed input MRI image $u_1^0$ to $u_N^0$ is then provided to the convolutional filters 213. This advantageously ensures that all jointly reconstructed scans are co-registered before the convolutional filtering by convolutional filters 213. This allows for shared edge information to be leveraged across all contrast.

In an exemplary embodiment, in each gradient descent step $GD^t$, trained functions are applied to the MRI images $u_1^{t-1}$ to $u_N^{t-1}$ using a neural network 211 and a forward-sampling operator 212, where at least one output MRI image $u^T$ is generated. The trained functions are applied to the MRI images $u_1^0$ to $u_N^0$ in at least a first step $GD^1$.

In each step GD, the forward-sampling operator determines an agreement between at least one MRI image $u_1^{t-1}$ to $u_N^{t-1}$ and the corresponding MRI measurement data set $f_1$ to $f_N$, for i=1 . . . N. In this example, the forward-sampling operator 212 determines an agreement between each MRI image $u_1^0$ to $u_N^0$ and a corresponding MRI measurement data set $f_1$ to $f_N$ individually.

As depicted in FIG. 2, the neural network 211 is a Convolutional Neural Network (CNN), where in each gradient descent step $GD^t$, a convolutional layer 213 mixes the transformed input MRI images $u^{t-1}$ to create a large number of output feature maps. Non-linear activation 214 and a second convolution 213 reduces the feature channels to the number of input MRI images. A data-fidelity term is computed individually for each input MRI image by a forward-sampling operator 212, where each forward model matrix $A_i$ contains a contrast specific under-sampling mask that may be varied between contrasts to enable complementary k-space sampling ($f_i$). In Wave-CAIPI acquisitions, $A_i$ additionally contains the Wave Point-Spread-Function (PSF) to account for the voxel spreading effect along the readout direction.

The multi-contrast (MC) Deep Learning (DL) mechanisms according to the disclosure may apply the following considerations for the reconstruction of a MRI image.

In an exemplary embodiment, in the MC DL reconstruction, each patch is processed one at a time.

In an exemplary embodiment, in the variational network of FIG. 2, the following two computations are performed sequentially in a plurality of gradient descent steps GD:

Filtering: 2D/3D convolutions 213 and non-linear activations 214 are applied to each image patch u. In contrast to single-contrast DL networks, the proposed method performs filtering operations on multiple contrasts simultaneously. This enables better differentiation between anatomical structures and aliasing artifacts resulting in sharper images with improved artifact/noise suppression.

Data-fidelity: For each contrast individually, the MRI forward model is computed, which includes point wise multiplication with the coil sensitivity C and summation over the collapsing voxel groups. In an exemplary embodiment, the MRI forward model may be computed in the k-space domain (e.g. by applying the Fourier transform and masking k-space, where samples that were acquired by the MR system are discarded). Next, the measured data f is subtracted and the Hermitian of the forward model applied. This includes pointwise multiplication with the conjugate of the sensitivity C and summation over the channels. Additionally, this data agreement is weighted by a contrast specific regularization parameter. If Wave-encoding is used, an additional pointwise multiplication with the PSF in hybrid space is performed.

In an exemplary embodiment, one or more inverse (transposed) translation and rotation transformations ($T^T R^T$) 216 are then performed after the convolutional filtering by convolutional filters 213 to transform each contrast/image back to its original image orientation to preserve agreement with the MR forward model computation (data term). For example, one or more inverse translation and rotation transformations ($T^T R^T$) 216 are applied to the output of the CNN 211 to transform each contrast/image of the output back to its original image orientation.

In these aspects, with the transformation(s) 215 and the inverse transformations 216, the jointly reconstructed scans are co-registered before the convolutional filtering to allow for shared edge information to be leveraged across all contrast, while the inverse transformation(s) 216 transform each contrast back to its respective original orientation to retain agreement with the MR forward model computation (data term).

Advantageously, with the transformation(s) 215 and the inverse transformations 216, only small additional computational overhead is required because the translation and rotation operations are applied to the coil-combined image data only (and not multichannel scanner data that has a data size that is at least 20 times larger than the coil-combined image data). This enables a wide adoption of the techniques of the disclosure, including using such techniques on low-cost scanners with limited computing power. A further advantage is that the transformation operations are applied during inference and do not affect the time consuming training of the deep learning network.

For each input MRI image $u_1^0$ to $u_N^0$, the inverse-transformed output of the CNN 211 and an output of the forward-sampling operator 212 is subtracted from the respective input MRI image $u_1^0$ to $u_N^0$.

A plurality of output MRI images $u_1^t$ to $u_N^t$ is provided as output of the gradient descent steps $GD^t$.

For the training of the MC DL network, we minimize the L2-loss of the difference image (network output image $u^T$—reference image g). Further refinement may be achieved by optimizing the network for each contrast image $u^T$ individually. Therefore, the MC DL architecture remains unchanged, only the loss function is evaluated for one contrast at a time. As a consequence, the reconstruction of N contrasts may require N DL networks. However, since the application/evaluation of the network is several orders of magnitude faster than the training, this redundancy barely affects the efficiency in clinical practice.

The one or more of the exemplary embodiments utilize DL to jointly reconstruct multiple clinical contrasts acquired with complementary k-space under-sampling and/or Wave-encoding using a variational network architecture that leverages the acquired MRI scanner data in the DL reconstruction (other network architectures should also work, however it is favorable to include a data fidelity term to enforce agreement with the scanner data). This was shown to benefit acquisitions with low signal-to-noise (SNR) ratio, where large over-smoothing and unnatural image appearance was prevented in contrast to the corresponding single-contrast method. High robustness towards low SNR is particularly useful for the implementation on clinical 1.5 T scanners, which have inherently lower SNR than 3 T systems.

A phase alignment step may be performed before the reconstruction to prevent large background phase variations between different contrasts.

When used with Wave-CAIPI, the Wave corkscrew may be varied for each contrast (e.g. by rotating the corkscrew around the readout (kx) axis and/or varying the number of cycles and/or gradient amplitude, etc.).

An individual network may be trained for each output contrast, in other words for each MRI protocol or MRI image.

According to various embodiments, the methods according to the disclosure may operate in image space, and/or on patches of image space. Predetermined under-sampling schemes may be used, in other words, i.e. the DL reconstruction may use predetermined MRI protocols/sequences.

For 3D imaging the DL reconstruction may be further refined using Wave-CAIPIRINHA sampling. Image patches may be selected in agreement with the sparse coupling pattern of Wave-encoding, which enables Wave-CAIPI reconstructions with DL also on low-end GPUs with moderate computation hardware (NVIDIA Titan XP).

Further examples of MRI reconstruction methods are described in U.S. application Ser. No. 16/857,908, filed Apr. 24, 2020, and in U.S. Provisional Application No. 62/838,458, filed Apr. 25, 2019, each of which is incorporated herein by reference in its entirety.

Accurate knowledge of the motion parameters (accounting for inter-scan motion) enables precise co-registration between the jointly reconstructed scans. In an exemplary embodiment, such parameters are obtained by registering the initial parallel imaging reconstructions, which typically exhibit residual aliasing artifacts but provide enough structural/anatomical information for accurate image registration, using, for example, FSL (Functional Magnetic Resonance Imaging of the Brain (FMRIB) Software Library) FLIRT (FMRIB's Linear Image Registration Tool). As illustrated in FIG. 4, exemplary embodiments substantially reduce aliasing artifacts in highly accelerated multi-contrast reconstructions.

One or more exemplary embodiments can be used with Wave-CAIPI (for 3D) or Bunch-Phase-Encoding (BPE) (for 2D), which modifies the k-space trajectory to introduce a voxel spreading effect along the readout. This improves the encoding of aliased voxels at high acceleration resulting in reduced artifacts and g-factor noise amplification. Advantageously, these advanced encoding techniques can be integrated synergistically into joint multi-contrast reconstructions, even in the presence of patient motion (see FIG. 4), given the image translation and rotation operations (and their inverse) retain the original image orientation of each contrast and hence do not affect the data term.

In one or more exemplary embodiments, a low-resolution background phase may be removed.

A background phase removal step improves high quality multi-contrast DL reconstructions.

Computation of coil sensitivity maps, e.g. using a ESPIRiT technique, as disclosed in the document Uecker, Martin, et al. "ESPIRiT—an eigenvalue approach to auto-calibrating parallel MRI: where SENSE meets GRAPPA." Magnetic resonance in medicine 71.3 (2014): 990-1001, may introduce a background phase in an initial SENSE reconstruction. This results in large phase variations between different contrasts.

FIG. 6 schematically illustrates varying under-sampling schemes of MRI protocols, according to aspects of the disclosure.

To improve the image quality of the MC DL reconstruction, the under-sampling scheme between different MRI protocols may be varied, ideally in a complementary fashion, which, in other words, means in a manner, wherein at least two under-sampling schemes are different from each other, in other words are not overlapping, and/or overlap of two under-sampling schemes is minimized, compared to two other under-sampling schemes. In another example, the under-sampling schemes of all MRI contrasts are different from each other, and/or an average overlap of all under-sampling schemes is minimized.

Referring to FIG. 5, in upper row 450, a first k-space under-sampling scheme is depicted, in middle row 460, a second k-space under-sampling scheme is depicted, and lower row 470, both under-sampling schemes 450 and 460 are depicted together to demonstrate the complementary characteristic of the under-sampling schemes.

As can be seen in FIG. 5, the k-space sampling points of the second scheme are arranged in distances, or unsampled spaces, between k-space sampling points of the first scheme, and/or have substantially equal distances k-space from the k-space sampling points of the first scheme, in other words, the two k-space sampling schemes complement each other to a regular k-space pattern.

FIG. 4 shows equally spaced/distributed lines in k-space, however the under-sampling schemes may comprise a random sampling pattern, which may provide even better MRI image quality.

Further, column 410 shows the under-sampling schemes in 2D, and column 420 shows the under-sampling schemes in 3D. In column 430, corresponding $G_y$ gradient variations, and in column 440, corresponding $G_z$ gradient variations, are depicted for each under-sampling schema. Therein, in row 450 the $G_y$ and the $G_z$ gradient variation have an offset of 0°, wherein in row 460 the $G_y$ and the $G_z$ gradient variation have an offset of 120°.

In general, the multi-contrast DL reconstruction may be improved by varying the under-sampling scheme among the different contrasts. Both in 2D and 3D a constant shift along ky and/or kz may be applied which results in a more complementary k-space sampling. Alternative strategies include CAIPIRINHA or random sampling as well as variations in the acceleration factor. If Wave-encoding is used, the Wave-CAIPI corkscrew may be additionally varied between contrasts, e.g. by adding a constant phase offset to the Gy and Gz gradient and/or by changing the gradient amplitude or gradient shape (number of sinusoidal cycles).

FIG. 6 illustrates a flow chart of a method for reconstructing a MRI image, according to aspects of the disclosure.

The method starts in step S10. In step S20, a plurality of MRI measurement data sets $f_1$ to $f_N$ are received, wherein each MRI measurement data set is acquired from an examination object based on a different MRI protocol of a MRI system. In step S30, MRI images $u_1^0$ to $u_N^0$ are received, which correspond to the MRI measurement data sets $f_1$ to $f_N$.

In step S40, one or more translation and rotation (TR) transformations 215 are performed on the input MRI images $u_1^0$ to $u_N^0$ to co-register the jointly reconstructed scans before the convolutional filtering. This allows for shared edge information to be leveraged across all contrast.

In step S50, the transformed input MRI images $u_1^0$ to $u_N^0$ are then provided to the neural network 211. For example, in at least a first step $GD^1$ (210), trained functions are applied to the transformed MRI images $u_1^0$ to $u_N^0$ using a neural network 211, and a forward-sampling operator 212. The forward-sampling operator 212 determines an agreement between at least one MRI image $u_1^0$ to $u_N^0$ and the corresponding MRI measurement data set $f_1$ to $f_N$. The output of the CNN 211 is then subjected to an inverse-transformation at step S60, and the inversely-transformed output and an output of the forward-sampling operator 212 is subtracted from the respective input MRI image $u_1^0$ to $u_N^0$ to generate at least one output MRI image $u^T$ at step S70. In step S80, the at least one output MRI image $u^T$ is provided. The method ends in step S90.

FIG. 7 illustrates a flow chart of a method for providing trained functions for reconstructing an MRI image, according to aspects of the disclosure.

The method starts in step T10. In step T20, a plurality of MRI measurement data sets $f_1$ to $f_N$ are received, wherein each data set is acquired from an examination object based on a different MRI protocol of a MRI system. In step T30, reference MRI images $g_1$ to $g_N$ are received, which are images with reduced MRI artefacts and/or noise amplification compared to the MRI images $u_1^0$ to $u_N^0$, each reference MRI images $g_1$ to $g_N$ corresponding to a respective one of MRI measurement data sets $f_1$ to $f_N$. In step T40, MRI images $u_1^0$ to $u_N^0$ are received corresponding to the MRI measurement data sets $f_1$ to $f_N$, wherein on each MRI measurement data set, a corresponding MRI image $u_1^0$ to $u_N^0$ is based. In step T45, before being provided to the neural network 211, one or more translation and rotation (TR) transformations 215 are performed on the input MRI images $u_1^0$ to $u_N^0$ to co-register the jointly reconstructed scans before the convolutional filtering. The transformed MRI images $u_1^0$ to $u_N^0$ are then subjected to the functions (e.g. convolution filtering 213 and non-linear activations 214) of the neural network 211 as discussed on step T50. In step T50, functions are applied to the MRI images $u_1^0$ to $u_N^0$ using a neural network 211 and a forward-sampling operator 212. Functions may be applied to the MRI images $u_1^0$ to $u_N^0$ in at least a first step $GD^1$, or in a number T of steps $GD^1$ to $GD^T$, wherein the forward-sampling operator determines an agreement between at least one MRI image $u_1^0$ to $u_N^0$ and the corresponding MRI measurement data set $f_1$ to $f_N$. In step T55, in an exemplary embodiment, the output of the neural network 211 may be subjected to an inverse-transformation, and the inversely-transformed output and an output of the forward-sampling operator 212 is subtracted from the respective input MRI image $u_1^0$ to $u_N^0$ to generate at least one output MRI image $u^T$. In step T60, a difference between the at least one output MRI image $u^T$ and the corresponding reference image $g_i$ is determined. In step T70, the functions are trained based on the determined difference, and, in step T80, the trained functions are provided. The method ends in step T90.

FIG. 8 illustrates a schematic drawing of a device 600 according to aspects of the disclosure.

The device, or computing device, 600 is configured for reconstructing an MRI image. In an exemplary embodiment, the computing device 600 comprises a memory 630, an interface 620, and at least one processing unit 610. In an exemplary embodiment, the processing unit 610 includes processor circuitry that is configured to perform one or more functions and/or operations of the processing unit 610, including controlling the operation of the device 600, and/or executing one or more instructions stored in memory 630. In an exemplary embodiment, the memory 630 contains instructions executable by the processing unit(s) 610, where execution of the instructions causes the computing device 600 to execute the following steps.

In a first step, a plurality of MRI measurement data sets $f_1$ to $f_N$ are received, wherein each MRI measurement data set is acquired from an examination object based on a different MRI protocol of a MRI system. In another step, MRI images $u_1^0$ to $u_N^0$ are received, which correspond to the MRI measurement data sets $f_1$ to $f_N$. In a further step, in at least a gradient descent step $GD^1$, trained functions are applied to the MRI images $u_1^0$ to $u_N^0$ using a neural network and a forward-sampling operator, wherein the forward-sampling operator determines an agreement between at least one MRI image $u_1^0$ to $u_N^0$ and the corresponding MRI measurement data set $f_1$ to $f_N$, wherein at least one output MRI image $u^T$ is generated. In a next step, the at least one output MRI image $u^T$ is provided.

From the above said, some general conclusions may be drawn:

Applying a variational model to the MRI images, may comprise the application of trained functions and the subtraction of a forward sampling operator. Thus, the step of applying, in at least a first step $GD^1$, trained functions to the MRI images $u_1^0$ to $u_N^0$, using a neural network (211) and a forward-sampling operator (212), may comprise applying a variational model to the MRI images $u_1^0$ to $u_N^0$, wherein, for each input MRI image $u_1^0$ to $u_N^0$, an output of the neural network and an output of the forward-sampling operator is subtracted from the respective input MRI image $u_1^0$ to $u_N^0$. Such a variational model allows for fast and efficient implementation in a computing environment, wherein it further provides high quality MRI image reconstructions.

The neural network may be a convolutional neural network in one or more exemplary embodiments, but is not limited thereto. Applying trained functions to the MRI images $u_1^0$ to $u_N^0$ may comprise applying a plurality of trained filter functions to the MRI images $u_1^0$ to $u_N^0$. The trained filter functions may be applied to the MRI images simultaneously, using convolutions 213 and non-linear activations 214. Each filter function may be applied to each MRI image $u_1^0$ to $u_N^0$. In an exemplary embodiment, before being provided to the neural network 211, one or more translation and rotation (TR) transformations 215 are performed on the input MRI images $u_1^0$ to $u_N^0$ to co-register the jointly reconstructed scans before the convolutional filtering. The transformed MRI images $u_1^0$ to $u_N^0$ are then subjected to the functions (e.g. convolution filtering 213 and non-linear activations 214) of the neural network 211. In an exemplary embodiment, the output of the neural network 211 may be subjected to an inverse-transformation, and the inversely-transformed output and an output of the forward-sampling operator 212 is subtracted from the respective input MRI image $u_1^0$ to $u_N^0$ to generate at least one output MRI image $u^T$.

For each of the MRI images $u_1^0$ to $u_N^0$ separately, the forward-sampling operator may determine an agreement, or in other words a similarity, between the MRI image $u_1^0$ to $u_N^0$ and the corresponding MRI measurement data sets $f_1$ to $f_N$ using a MRI forward model of the corresponding MRI protocol. The output of the forward-sampling operator may be in the image domain. The agreement may also be referred to as output of the forward-sampling operator, agreement term, or data-fidelity term, and ensures an agreement of the current MR image $u_i^{t-1}$ to $u_i^{t-1}$, which is the input image of a step $GD^t$ with the underlying MRI measurement data set for $i=1 \ldots N$.

The methods may further comprise receiving coil sensitivities C of the MRI system, and/or receiving an under-sampling scheme for each MRI protocol. Accordingly, the forward-sampling operator may determine the agreement between a respective MRI image $u_1^0$ to $u_N^0$ and the corresponding MRI measurement data set $f_1$ to $f_N$ using a MRI forward model of the MRI protocol, and/or based on the coil sensitivities C and/or the respective under-sampling scheme. Taking into account the above additional inputs greatly improves accuracy of the ML algorithms.

Applying, in at least one step $GD^1$, trained functions to the MRI images $u_1^0$ to $u_N^0$ may comprise applying, in a plurality of steps $GD^1$ to $GD^T$ for a predefined number T, trained functions to the MRI images $u_1^0$ to $u_N^0$. The trained functions in each step GD may comprise filter functions, which are based on trained filter parameters specific to each step GD. In an exemplary embodiment, before being provided to the neural network 211, one or more translation and rotation (TR) transformations 215 are performed on the input MRI images $u_1^0$ to $u_N^0$ to co-register the jointly reconstructed scans before the convolutional filtering. The transformed MRI images $u_1^0$ to $u_N^0$ are then subjected to the functions (e.g. convolution filtering 213 and non-linear activations 214) of the neural network 211. In an exemplary embodiment, the output of the neural network 211 may be subjected to an inverse-transformation, and the inversely-transformed output and an output of the forward-sampling operator 212 is subtracted from the respective input MRI image $u_1^0$ to $u_N^0$ to generate at least one output MRI image $u^T$.

Therein each step $GD^t$ for $t=1 \ldots T$ may comprise receiving input MRI images $u_1^{t-1}$ to $u_N^{t-1}$, applying trained functions to the MRI images $u_1^{t-1}$ to $u_N^{t-1}$, using the neural network, and the forward-sampling operator, wherein MRI output images $u_1^t$ to $u_N^t$ are generated, and providing the MRI output images $u_i^t$ to $u_N^t$, wherein in particular in case that another step GD is following, the output images may be provided to the following step GD as input images until step $GD^T$ has been executed.

Using the above ML algorithms with a plurality of filtering steps GD, a variational network with improved performance and MRI image quality may be provided, as the underlying MRI measurement data sets are taken into account in an advantageous manner within the algorithms.

Applying trained functions to the input MRI images $u_1^{t-1}$ to $u_N^{t-1}$ may comprise applying the neural network 211 and the forward-sampling operator 212 on the input MRI images $u_1^{t-1}$ to $u_N^{t-1}$, and subtracting, for each input MRI image $u_1^{t-1}$ to $u_N^{t-1}$, an corresponding output of the neural network 211 and output of the forward-sampling operator 212 from the input MRI image $u_1^t$ to $u_N^t$.

Therein, the output terms of the neural network 211 and the forward-sampling operator 212 may be associated with artefact terms of the respective current MR image in a filtering step GD. Therefore, it is apparent for a person skilled in the art, that general subtracting operations, and also general adding operations and other operations of relevance may be used to take into account these artefact terms with regard to the current MRI input images in each step $GD^T$.

The forward-sampling operator may determine an agreement between each MRI image $u_i^{t-1}$, with $i=0 \ldots N$, and the corresponding MRI measurement dataset $f_i$, using the relation $\lambda_i^{t-1} A^*_i (A_i u_i^{t-1} - f_i)$, wherein $\lambda_i^{t-1}$ is a contrast specific regularization parameter, $A_i$ is a MRI forward model for the corresponding MRI protocol. Such operations further improve efficiency and MRI image quality of the ML algorithms, and $A^*_i$ is an adjoint of the MRI forward model $A_i$.

The MRI measurements data sets $f_1$ to $f_N$ may be based on different MRI contrasts of the MRI system, and accordingly, the MRI images $u_1^0$ to $u_N^0$ may be MRI images with different contrasts of the examination object. Thereby, a joint reconstruction of multiple MRI images of a patient may be enabled, as often required in clinical practice.

The techniques according to the disclosure may be based on or applied to a WAVE-CAIPI MRI technique, i.e. to 2D and volumetric Wave-CAIPI imaging, in particular MRI measurement data sets $f_1$ to $f_N$ may be acquired based on WAVE-CAIPI MRI protocols with different contrasts. Combining WAVE-CAIPI techniques with the described ML reconstruction techniques provides particularly good results in MRI image reconstruction.

The at least one output MRI image $u^T$ may comprise a plurality of output MRI images $u_1^T$ to $u_N^T$. For example, the at least one output MRI image $u^T$ may be a single output image $u_i^T$, for $i=\{1 \ldots N\}$, chosen of a plurality of output MRI images $u_1^T$ to $u_N^T$, wherein each output MRI image $u_1^T$ to $u_N^T$ corresponds to a respective one of the MRI images $u_1^0$ to $u_N^0$. Such a reduction to only one output image is advantageously faster, when a specific MRI contrast, or MRI protocol, is of particular interest, such that MRI image reconstruction is to be optimized for that MRI protocol.

MRI measurement data sets $f_1$ to $f_N$ may be undersampled in k-space based on a specific under-sampling scheme, in various embodiments, each data set may be undersampled. Applying the principles of the disclosure to reconstructing undersampled MRI measurement data, has high relevance for medical examinations.

At least two of the MRI measurement data sets $f_1$ to $f_N$ may be based on different under-sampling schemes, in various embodiments, all MRI measurement data sets $f_1$ to $f_N$ may be based on different under-sampling schemes. The different under-sampling schemes may be complementary under-sampling schemes. Thereby, the ML reconstruction algorithm is able to provide even higher quality MRI images.

Reconstructing MRI images $u_1^0$ to $u_N^0$ from the MRI measurement data sets $f_1$ to $f_N$ may further comprise removing a low-resolution background phase from the MRI images $u_1^0$ to $u_N^0$, prior to applying the trained filter functions to the images. Such, further improvements to image quality and efficiency of the ML algorithms are enabled.

Applying trained functions to the MRI images $u_1^0$ to $u_N^0$ may further comprise dividing the coil sensitivities C, the MRI measurement data sets $f_1$ to $f_N$, the MRI images $u_1^0$ to $u_N^0$, and the reference images $g_1$ to $g_N$ into patches of collapsing voxel groups, and applying the trained functions to the patches of collapsing voxel groups of each MRI image $u_1^0$ to $u_N^0$ individually. In such a way, efficiency of the ML reconstruction algorithms are further improved, in other words resources of a processing unit and memory may be used more efficiently.

Summarizing, in the field of MRI, a Multi-Contrast (MC) Deep Learning (DL) MRI image reconstruction is provided, wherein a plurality of MRI measurement data sets $f_1$ to $f_N$ and corresponding initially reconstructed MRI images $u_1^0$ to $u_N^0$ are provided. In a variational network, trained functions and a forward-sampling operator are applied to the MRI images $u_1^0$ to $u_N^0$, using a Convolutional Neural Network (CNN), wherein the forward-sampling operator determines an agreement between at least one MRI image $u_1^0$ to $u_N^0$ and the corresponding MRI measurement data set $f_1$ to $f_N$. At least one output MRI image $u^T$ is generated.

Thereby, the improved method according to the disclosure provides a shorter total measurement time for an MRI image in a clinical application and at the same time improved MRI image quality, resulting in more reliable medical diagnoses in clinical applications.

Although the disclosure has been shown and described with respect to certain preferred aspects, equivalents and modifications will occur to others skilled in the art upon the reading and understanding of the specification. The present disclosure includes all such equivalents and modifications and is limited only by the scope of the appended claims.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

Some embodiments of the present disclosure generally provide for a plurality of circuits or other electrical devices such as processors. All references to the circuits and other electrical devices and the functionality provided by each are not intended to be limited to encompassing only what is illustrated and described herein. While particular labels may be assigned to the various circuits or other electrical devices disclosed, such labels are not intended to limit the scope of operation for the circuits and the other electrical devices. Such circuits and other electrical devices may be combined with each other and/or separated in any manner based on the particular type of electrical implementation that is desired. It is recognized that any circuit or other electrical device disclosed herein may include any number of microcontrollers, a graphics processor unit (GPU), integrated circuits, memory devices (e.g., FLASH, random access memory (RAM), read only memory (ROM), electrically programmable read only memory (EPROM), electrically erasable programmable read only memory (EEPROM), or other suitable variants thereof), and software which co-act with one another to perform operation(s) disclosed herein. In addition, any one or more of the electrical devices may be configured to execute a program code that is embodied in a non-transitory computer readable medium programmed to perform any number of the functions as disclosed.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A computer-implemented method for reconstructing a magnetic resonance imaging (MRI) image, comprising:
   receiving a plurality of MRI measurement data sets $f_1$ to $f_N$, wherein each data set is acquired from an examination object based on a different MRI protocol of an MRI system;
   receiving MRI images $u_1^0$ to $u_N^0$ corresponding to the MRI measurement data sets $f_1$ to $f_N$; and
   in at least a first step $GD^1$:
      performing one or more translation and rotation transformations on the MRI images $u_1^0$ to $u_N^0$;
      applying one or more trained functions (i) to the transformed MRI images $u_1^0$ to $u_N^0$, using a neural network, and (ii) to the MRI images $u_1^0$ to $u_N^0$, using a forward-sampling operator;
      wherein an output of the neural network comprises a result of filtering the transformed MRI images $u_1^0$ to $u_N^0$ via the one or more trained functions based upon a data-fidelity term that is computed individually by the forward-sampling operator for each one of the MRI images $u_1^0$ to $u_N^0$;
      performing one or more inverse translation and rotation transformations on the output of the neural network to transform each of the MRI images $u_1^0$ to $u_N^0$ back to an original image orientation to preserve agreement with the forward-sampling operator;
      generating at least one output MRI image $u^T$ based on an output of the forward-sampling operator, the inversely transformed output of the neural network, and the input MRI images $u_1^0$ to $u_N^0$; and
      providing the at least one output MRI image $u^T$.

2. The computer-implemented method according to claim 1, wherein the forward-sampling operator determines an agreement between at least one MRI image $u_1^0$ to $u_N^0$ and the corresponding MRI measurement data set $f_1$ to $f_N$.

3. The computer-implemented method according to claim 1, wherein applying trained functions to the MRI images $u_1^0$ to $u_N^0$ comprises:
   applying an unrolled model to the MRI images $u_1^0$ to $u_N^0$, wherein, for each input MRI image $u_1^0$ to $u_N^0$, an output of the neural network and an output of the forward-sampling operator is subtracted from the respective input MRI image $u_1^0$ to $u_N^0$ to generate the at least one output MRI image $u^T$.

4. The computer-implemented method according to claim 1, wherein the neural network is a convolutional neural network, and wherein applying trained functions to the MRI images $u_1^0$ to $u_N^0$ comprises:
   applying a plurality of trained filter functions to the MRI images $u_1^0$ to $u_N^0$ simultaneously, using convolutions and non-linear activations, wherein each filter function is applied to each MRI image $u_1^0$ to $u_N^0$.

5. The computer-implemented method according to claim 1, wherein, for each of the MRI images $u_1^0$ to $u_N^0$ separately, the forward-sampling operator determines an agreement between each of the MRI images $u_1^0$ to $u_N^0$ and the corresponding MRI measurement data sets $f_1$ to $f_N$ using a MRI forward model of the corresponding MRI protocol.

6. The computer-implemented method according to claim 1, further comprising:
   receiving coil sensitivities C of the MRI system; and
   receiving an under-sampling scheme for each MRI protocol,
   wherein, the forward-sampling operator determines an agreement between a respective MRI image $u_1^0$ to $u_N^0$ and the corresponding MRI measurement data set $f_1$ to $f_N$ using a MRI forward model of the MRI protocol, based on the coil sensitivities C and the respective under-sampling scheme.

7. The computer-implemented method according to claim 1, wherein applying the trained functions to the MRI images $u_1^0$ to $u_N^0$ comprises:
   applying, in a plurality of steps $GD^1$ to $GD^T$ for a predefined number T, trained functions to the MRI images $u_1^0$ to $u_N^0$, each step $GD^t$ for $t=1 \ldots T$ comprising:
   receiving input MRI images $u_1^{t-1}$ to $u_N^{t-1}$;
   applying trained functions: to transformations of the MRI images $u_1^{t-1}$ to $u_N^{t-1}$, using the neural network, to generate the output of the neural network, and to the MRI images $u_1^{t-1}$ to $u_N^{t-1}$, using the forward-sampling operator, to generate the output of the forward-sampling operator, wherein MRI output images $u_i^t$ to $u_N^t$ are generated based on the output of the neural network and the output of the forward-sampling operator; and
   providing the MRI output images $u_1^t$ to $u_N^t$.

8. The computer-implemented method according to claim 7, wherein generating the MRI output images $u_1^t$ to $u_N^t$ comprises:
   subtracting, for each input MRI image $u_1^{t-1}$ to $u_N^{t-1}$, an corresponding output of the neural network and output of the forward-sampling operator from the input MRI image $u_1^t$ to $u_N^t$.

9. The computer-implemented method according to claim 1, wherein the forward-sampling operator determines an agreement between each MRI image $u_i^{t-1}$, with $i=0 \ldots N$, and the corresponding MRI measurement dataset $f_i$, using the relation:
   $\lambda_i^{t-1} A^*_i (A_i u_i^{t-1} - f_i)$,
   wherein $\lambda_i^{t-1}$ is a contrast specific regularization parameter, $A_i$ is a MRI forward model for the corresponding MRI protocol, and $A^*_i$ is an adjoint of the MRI forward model $A_i$.

10. The computer-implemented method according to claim 1, wherein the MRI measurements data sets $f_1$ to $f_N$ are based on different MRI contrasts of the MRI system.

11. The computer-implemented method according to claim 1, wherein the MRI measurement data sets $f_1$ to $f_N$ are acquired based on MRI protocols with different contrasts.

12. The computer-implemented method according to claim 1, wherein the at least one output MRI image $u^T$ is an output image $u_i^T$, for i={1 ... N}, of a plurality of output MRI images $u_1^T$ to $u_N^T$, wherein each output MRI image $u_1^T$ to $u_N^T$ corresponds to a respective one of the MRI images $u_1^0$ to $u_N^0$.

13. The computer-implemented method according to claim 1, wherein each MRI measurement data set $f_1$ to $f_N$ is undersampled in k-space based on a specific under-sampling scheme.

14. The computer-implemented method according to claim 9, wherein at least two of the MRI measurement data sets $f_1$ to $f_N$ are based on different under-sampling schemes.

15. The computer-implemented method according to claim 1, wherein reconstructing MRI images $u_1^0$ to $u_N^0$ from the MRI measurement data sets $f_1$ to $f_N$ further comprises:
removing a low-resolution background phase from the MRI images $u_1^0$ to $u_N^0$.

16. The computer-implemented method according to claim 1, wherein applying trained functions to the MRI images $u_1^0$ to $u_N^0$ further comprises:
dividing coil sensitivities C of the MRI system, the MRI measurement data sets $f_1$ to $f_N$, the MRI images $u_1^0$ to $u_N^0$, and reference images $g_1$ to $g_N$ into patches of collapsing voxel groups, and
applying the trained functions to the patches of collapsing voxel groups of each MRI image $u_1^0$ to $u_N^0$ individually.

17. The computer-implemented method according to claim 1, wherein reconstructing MRI images $u_1^0$ to $u_N^0$ further comprises registering initial parallel imagining reconstructions of the MRI images $u_1^0$ to $u_N^0$ to determine motion parameters associated with inter-scan motion to increase co-registration between jointly reconstructed scans.

18. A computer configured for reconstructing an MRI image, the computer comprising:
a memory storing executable instructions;
an interface; and
a processor configured to execute the instructions to cause the computer to:
receive, by the interface, a plurality of MRI measurement data sets $f_1$ to $f_N$, wherein each data set is acquired from an examination object based on a different MRI protocol of an MRI system;
receive, by the interface, MRI images $u_1^0$ to $u_N^0$ corresponding to the MRI measurement data sets $f_1$ to $f_N$; and
in at least a first step $GD^1$:
perform, by the processor, one or more translation and rotation transformations on the MRI images $u_1^0$ to $u_N^0$;
apply, by the processor, one or more trained functions (i) to the transformed MRI images $u_1^0$ to $u_N^0$, using a neural network, and (ii) to the MRI images $u_1^0$ to $u_N^0$, using a forward-sampling operator;
wherein an output of the neural network comprises a result of filtering the transformed MRI images $u_1^0$ to $u_N^0$ via the one or more trained functions based upon a data-fidelity term that is computed individually by the forward-sampling operator for each one of the MRI images $u_1^0$ to $u_N^0$;
perform, by the processor, one or more inverse translation and rotation transformations on the output of the neural network to transform each of the MRI images $u_1^0$ to $u_N^0$ back to an original image orientation to preserve agreement with the forward-sampling operator;
generate, by the processor, at least one output MRI image $u^T$ based on an output of the forward-sampling operator, the inversely transformed output of the neural network, and the input MRI images $u_1^0$ to $u_N^0$; and
provide, by the interface, the at least one output MRI image $u^T$.

19. The computer according to claim 18, wherein the forward-sampling operator determines an agreement between at least one MRI image $u_1^0$ to $u_N^0$ and the corresponding MRI measurement data set $f_1$ to $f_N$.

20. The computer according to claim 18, wherein execution of the instructions further causes the computer to:
receive reference MRI images $g_1$ to $g_N$ with reduced MRI artefacts or noise amplification compared to the MRI images $u_1^0$ to $u_N^0$, corresponding to the MRI measurement data sets $f_1$ to $f_N$;
determine a difference between the at least one output MRI image $u^T$ and the corresponding reference image $g_i$, i={1 ... N};
train the functions based on the determined difference; and
provide the trained functions.

21. The computer-implemented method according to claim 1, wherein applying trained functions to the MRI images $u_1^0$ to $u_N^0$ comprises applying the trained functions only to coil-combined image data.

22. The computer-implemented method according to claim 1, wherein applying trained functions to the MRI images $u_1^0$ to $u_N^0$ comprises applying the trained functions applying the trained functions individually to patches of collapsing voxel groups of each MRI image $u_1^0$ to $u_N^0$.

23. The computer-implemented method according to claim 1, wherein the data-fidelity term is computed individually for each input MRI image by the forward-sampling operator in accordance with a set of forward model matrices.

24. The computer-implemented method according to claim 23, wherein each one of the set of forward model matrices contains a contrast specific under-sampling mask that is varied between contrasts to enable complementary k-space sampling.

* * * * *